US008278087B2

(12) United States Patent
Remmereit et al.

(10) Patent No.: US 8,278,087 B2
(45) Date of Patent: Oct. 2, 2012

(54) ENERGY PRODUCTION WITH HYPERTHERMOPHILIC ORGANISMS

(75) Inventors: Jan Remmereit, Volda (NO); Michael Thomm, Regensburg (DE)

(73) Assignee: The University of Regensburg, Regensburg (DE)

( * ) Notice: Subject to any disclaimer, the term of this patent is extended or adjusted under 35 U.S.C. 154(b) by 70 days.

(21) Appl. No.: 12/566,282

(22) Filed: Sep. 24, 2009

(65) Prior Publication Data

US 2010/0093046 A1    Apr. 15, 2010

Related U.S. Application Data

(63) Continuation-in-part of application No. 11/879,710, filed on Jul. 18, 2007.

(60) Provisional application No. 61/099,750, filed on Sep. 24, 2008, provisional application No. 61/122,573, filed on Dec. 15, 2008, provisional application No. 61/233,644, filed on Aug. 13, 2009, provisional application No. 60/831,635, filed on Jul. 18, 2006.

(51) Int. Cl.
*C12M 1/00* (2006.01)
(52) U.S. Cl. ........ 435/243; 435/471; 435/41; 435/290.1
(58) Field of Classification Search .................. None
See application file for complete search history.

(56) References Cited

U.S. PATENT DOCUMENTS

| | | | |
|---|---|---|---|
| 3,676,363 | A | 7/1972 | Mosier |
| 4,530,956 | A | 7/1985 | Ugelstad |
| 4,787,455 | A | 11/1988 | Snavely, Jr. |
| 4,986,353 | A | 1/1991 | Clark |
| 4,986,354 | A | 1/1991 | Cantu |
| 5,000,000 | A | 3/1991 | Ingram et al. |
| 5,354,878 | A | 10/1994 | Connemann |
| 5,661,017 | A | 8/1997 | Dunahay |
| 5,910,254 | A | 6/1999 | Guelcher |
| 6,000,551 | A | 12/1999 | Kanel |
| 6,299,774 | B1 | 10/2001 | Ainsworth |
| 6,524,486 | B2 | 2/2003 | Borodyanski |
| 2004/0121447 | A1 | 6/2004 | Fournier |
| 2005/0061737 | A1* | 3/2005 | Linden et al. .............. 210/602 |
| 2005/0064577 | A1 | 3/2005 | Berzin |

FOREIGN PATENT DOCUMENTS

| | | |
|---|---|---|
| EP | 0193369 | 9/1986 |
| EP | 0656459 | 6/1995 |
| JP | 08308587 | 11/1996 |
| JP | 2003326237 | 11/2003 |
| WO | 96/27070 | 9/1996 |
| WO | 97/45625 | 12/1997 |
| WO | 99/19375 | 4/1999 |
| WO | 99/36667 | 7/1999 |
| WO | 99/54592 | 10/1999 |
| WO | 02/06503 | 1/2002 |
| WO | 2006056819 | 6/2006 |
| WO | 2008/053353 | 5/2008 |

OTHER PUBLICATIONS

Vazhappilly et al. "Heterotrophic Production Potential of Omega-3 Polyunsaturated Fatty Acids by Microalgae and Algae-like Microorganisms" Botanica Marina vol. 41, 1998, pp. 553-558.*
Santangelo, Thomas J., et al., "Shuttle Vector Expression in Thermococcus kodakaraensis: Contributions of cis Elements to Protein Synthesis in a Hyperthermophilic Archaeon," Applied and Environmental Microbiology, May 2008, pp. 3099-3104.
Waege, Ingrid, "Shuttle vector-based transformation system for Pyrococcus furiosus," Applied and Environmental Microbiology, May 2010, vol. 76, No. 10, pp. 3808-3313.
Lucas, Soizick, et al., "Construction of a shuttle vector for, and spheroplast transformation of, the hyperthermophilic Archaeon Pyrococcus abyssi," Applied and Environmental Microbiology, Nov. 2002, vol. 68, No. 11, pp. 5528-5536.
Hethke, Carina, et al., "A cell-free transcription system for the hyperthermophilic archaeon Pyrococcus furiosus," Nucleic Acids Research, Jun. 15, 1996, vol. 24, No. 12, Jun. 15, 1996, pp. 2369-2376.
Large, Andrew, "Characterization of a tightly controlled promoter of the halophilic archaeon Haloferax volcanii and its use in the analysis of the essential cct1 gene," Molecular Microbiology, Dec. 2007, vol. 66, No. 5, pp. 1092-1106.
Bringer-Meyer et al., (1986), "Pyruvate decarboxylase from Zymomonas mobilis. Isolation and partial characterization" Arch. Microbiol. 146:105-110.
Brau et al., (1986), "Cloning and expression of the structural gene for pyruvate decarboxylase of Zymomonas mobilis in Escherichia coli." Arch. Microbiol. 144:296-301.
Chinese Office Action dated Aug. 30, 2010 from CN Patent Application No. 200780030825.6.
Chou, et al., "Hydrogenesis in hyperthermophilic microorganisms: Implications for Biofuels," Metabolic Engineering, vol. 10, Jun. 28, 2008, pp. 394-404.
Conway et al., (1987), "Cloning and sequencing of the alcohol dehydrogenase II gene from Zymomonas mobilis." J. Bacteriol. 169:2591-2597.
Conway et al., (1987), "Promoter and nucleotide sequences of the Zymomonas mobilis pyruvate decarboxylase." J. Bacteriol. 169:949-954.
Eichler, Jerry; "Biotechnological uses of archaeal extremozymes"; Biotechnology Advances (2001); vol. 19, pp. 261-278.
Eriksen, et al., "Hydrogen production in anaerobic and microaerobic thermotoga neapolitana," Biotechnology Letters, vol. 30, Sep. 12, 2007, pp. 103-109.
Examiner's First Report on AU Patent Application No. 2007315860 dated Feb. 23, 2010.
Ingram et al., (1987), "Genetic engineering of ethanol production in Escherichia coli." Appl. Environ. Microbiol. 53:2420-2425.

(Continued)

*Primary Examiner* — Blaine Lankford, Jr.
*Assistant Examiner* — Lauren K Van Buren
(74) *Attorney, Agent, or Firm* — Casimir Jones SC

(57) ABSTRACT

The present invention relates to the field of degradation with hyperthermophilic organisms, and in particular to the use of hyperthermophilic degradation to produce heat and energy rich components including hydrogen and ethanol from a biomass. In some embodiments, a biomass is fermented in the presence of hyperthermophilic organisms to produce heat. The heat is used to heat a liquid which is used directly in a heat pump or radiant heat or to produce electricity or drive a steam turbine. In some embodiments, acetate is utilized as a substrate to produce energy by methanogenesis.

15 Claims, 7 Drawing Sheets

OTHER PUBLICATIONS

Ingram et al., (1988), "Expression of Different Levels of Ethanologenic Enzymes from *Zymomonas mobilis* in Recombinant Strains of *Escherichia coli*." Appl. Environ. Microbiol. 54:397-404.

International Search Report dated Jan. 15, 2009, International Patent Application No. PCT/IB2007/003772.

Kanai, T., et al., "Continuous Hydrogen Production by the Hyperthermophilic Archaeon," Thermococcus Kodakaraensis KOD1, Journal of Biotechnology, Elsevier Science Publishers, Amsterdam, NL, vol. 116, No. 3, Mar. 30, 2005, pp. 271-282.

Kengen, et al., "Growth and energy conservation in batch cultures of pyrococus furiosus," FEMS Microbiology Letters, vol. 117, 1994, pp. 305-310.

Neale et al., (1987), "Nucleotide sequence of the pyruvate decarboxylase gene from *Zymomonas mobilis*." Nucleic Acid. Res. 15:1753-1761.

van Groenestijn, J.W., et al.; "Energy aspects of biological hydrogen production in high rate bioreactors operated in the thermophilic temperature range"; International Journal of Hydrogen Energy (2002); vol. 27, pp. 1141-1147.

Woodward, et al., "Efficient hydrogen production using enzyes of the pentose phosphate pathway," Proceedings of the 2002 U.S. DOE hydrogen program review (2002), pp. 1-12.

Tamotsu, Kanai, et al.; "Continuous hydrogen production by the hyperthermophilic archaeon, Thermococcus Kodakaraensis KOD1"; Journal of Biotechnology (2005); Vo. 116, pp. 271-282.

English language machine translation of JP 08-308587 (Nov. 26, 1996).

English language machine translation of JP 2003-326237 (Nov. 18, 2003).

\* cited by examiner

ENERGY PRODUCTION WITH HYPERTHERMOPHILIC ORGANISMS

CROSS REFERENCE TO RELATED APPLICATIONS

This application claims the benefit of U.S. Prov. Appl. Nos. 61/099,750 filed Sep. 24, 2008, 61,122,573, filed Dec. 15, 2008 and 61/233,644, filed Aug. 13, 2009, and is a continuation-in-part of U.S. application Ser. No. 11/879,710 (pending) filed Jul. 18, 2007, which claims the benefit of U.S. Prov. Appl. No. 60/831,635 filed Jul. 18, 2006, all which are incorporated by reference herein in their entirety.

FIELD OF THE INVENTION

The present invention relates to the field of degradation of biomass or other organic matter with hyperthermophilic organisms, and in particular to the use of hyperthermophilic degradation to produce heat, ethanol, hydrogen and other energy substrates from a biomass or other organic matter.

BACKGROUND OF THE INVENTION

The cost of conventional energy sources has increased dramatically in the last few years, and the use of many conventional energy sources such as oil, coal and nuclear power has been demonstrated to be harmful to the environment.

Many clean alternative energy sources have been developed or proposed. Such sources include solar energy, geothermal energy, wind energy, hydroelectric energy, hydrogen reactors and fuel cells. However, many of these sources are either expensive (solar energy) or limited by geographical concerns (geothermal, wind and hydropower).

Other alternative energy sources make use of biomass. However, those systems often involve the production of a secondary product such as ethanol or involve combusting the materials. These methods suffer from problems including contamination of the environment and requiring the use of valuable farmland to produce biomass.

Accordingly, what is needed in the art is alternative systems to utilize waste biomass materials or naturally available biomass materials to produce heat or electricity.

SUMMARY OF THE INVENTION

The present invention relates to the field of degradation with hyperthermophilic organisms, and in particular to the use of hyperthermophilic degradation to produce heat, ethanol, hydrogen and other energy substrates from a biomass. In some embodiments, the present invention provides a system comprising: a bioreactor, the bioreactor containing biomass and a population of at least one genus of hyperthermophilic organisms; and an energy transfer system. In some embodiments, the hyperthermophilic organisms are anaerobic hyperthermophilic organisms. In some preferred embodiments, the anaerobic hyperthermophilic organisms are selected from the group consisting of the genera *Pyrococcus, Thermococcus, Palaeococcus, Acidianus, Pyrobaculum, Pyrodictium, Pyrolobus, Methanopyrus, Methanothermus*, hyperthermophilic Methanococci like *Mc. jannaschii, Fervidobacterium* and *Thermotoga*, and combination thereof. In other embodiments, the hyperthermophilic organisms are aerobic hyperthermophilic organisms selected from the genera *Thermus, Bacillus, Geobacillis* and *Thermoactinomyces*. In still other embodiments, the aerobic hyperthermophilic organisms are selected from the group consisting of *Aeropyrum pernix, Metallosphaera sedula* and other *Metallosphaera* species *Sulfolobus solfataricus, Sulfolobus tokodaii, Thermoplasma acidophilum* and *Thermoplasma volcanium*, and combinations thereof. In some embodiments, the biomass is supplemented with a cell culture media component selected from the group consisting of a mineral source, vitamins, amino acids, an energy source, and a microorganism extract.

In some embodiments, the energy transfer system is selected from the group consisting of a fuel cell, a combustion unit, a thermocouple, and a heat transfer system. In further embodiments, the combustion unit comprises a steam powered system. In still further embodiments, the steam powered system is a steam turbine or generator. In some embodiments, the heat transfer system comprises a heat pump. In some embodiments, the energy transfer system is a thermocouple and wherein the energy transfer system further comprises an electrolysis system that coverts water into hydrogen and oxygen. In some preferred embodiments, the biomass is selected from the group consisting of sewage, agricultural waste products like corn steep liquor and soybean hulls, brewery grain by-products, food waste, organic industry waste, forestry waste, crops, grass, seaweed, plankton, algae, fish, fish waste, dairy residues such as whey, cellulose and cellulose and/or lignocellulosic containing materials such as wood, grass shrubs, perennial crops or annual crops, cellulose and cellulose and/or lignocellulosic containing waste products such as scrap wood, reclaimed wood, sawdust, waste materials from potato, sugar cane, corn and/or sugar beet processing, residual material from biogas production, for example corn and corn/manure mixtures, residues from silage, and combinations thereof.

In some embodiments, the present invention provides methods comprising: a) providing a biomass and a population of at least one genus of a hyperthermophilic organism; b) fermenting the biomass in the presence of the population of at least one genus of a hyperthermophilic organism under conditions such that heat is produced; c) using the heat to produce electricity or heat a liquid. In some embodiments, the hyperthermophilic organisms are anaerobic hyperthermophilic organisms. In some preferred embodiments, the anaerobic hyperthermophilic organisms are selected from the group consisting of the genera *Pyrococcus, Thermococcus, Palaeococcus, Acidianus, Pyrobaculum, Pyrodictium, Pyrolobus, Methanopyrus, Methanothermus*, hyperthermophilic Methanococci like *Mc. jannaschii, Fervidobacterium*, and *Thermotoga*, and combinations thereof. In other embodiments, the hyperthermophilic organisms are aerobic hyperthermophilic organisms selected from the genera *Thermus, Bacillus*, and *Thermoactinomyces*. In still other embodiments, the aerobic hyperthermophilic organisms are selected from the group consisting of *Aeropyrum pernix, Sulfolobus solfataricus, Metallosphaera sedula, Sulfobus tokodaii, Thermoplasma acidophilum* and *Thermoplasma volcanium*, and combinations thereof. In some preferred embodiments, the biomass is selected from the group consisting of sewage, agricultural waste products like corn steep liquor and soybean hulls, brewery grain by-products, food waste, organic industry waste, forestry waste, crops, grass, seaweed, plankton, algae, fish, fish waste, and combinations thereof. In some embodiments, the biomass is supplemented with a cell culture media component selected from the group consisting of a mineral source, vitamins, amino acids, an energy source, and a microorganism extract.

In some embodiments, the liquid is water and the heating produces steam. In some embodiments, the steam is used to drive a steam turbine to produce electricity. In further embodiments, the heated liquid is transferred to a building for radiant heat. In some embodiments, the electricity is produced via a thermocouple. In further embodiments, the electricity is used for electrolysis of water. In some embodiments, the liquid is transferred to a heat pump.

In some embodiments, the present invention further provides methods comprising: a) providing a biomass and a population of at least one genus of a hyperthermophilic organism; and b) degrading the biomass in the presence of the population of at least one genus of a hyperthermophilic organism under conditions such that degradation products are produced. In some preferred embodiments, the anaerobic hyperthermophilic organisms are selected from the group consisting of the genera *Pyrococcus, Thermococcus, Palaeococcus, Acidianus, Pyrobaculum, Pyrolobus, Pyrodictium, Methanopyrus, Methanothermus*, hyperthermophilic Methanococci like *Methanocaldococcus jannaschii, Fervidobacterium* and *Thermotoga*, and combinations thereof. In other embodiments, the hyperthermophilic organisms are aerobic hyperthermophilic organisms selected from the genera *Thermus, Bacillus*, and *Thermoactinomyces*. In still other embodiments, the aerobic hyperthermophilic organisms are selected from the group consisting of *Aeropyrum pernix, Sulfolobus solfataricus, Sulfobus tokodaii, Metallosphaera sedula, Thermoplasma acidophilum* and *Thermoplasma volcanium*, and combinations thereof. In some preferred embodiments, the biomass is selected from the group consisting of sewage, agricultural waste products, brewery grain by-products, food waste, organic industry waste, forestry waste, crops, grass, seaweed, especially brown algae, plankton, algae, fish, fish waste, and combinations thereof. In some embodiments, the biomass is supplemented with a cell culture media component selected from the group consisting of a mineral source, vitamins, amino acids, an energy source, and a microorganism extract. In some further preferred embodiments, the degradation products are selected from the group consisting of hydrogen, methane and ethanol. In some embodiments, the methods further comprise the step of converting the degradation products into energy. In some embodiments, the methods further comprise the step of using the hydrogen in a fuel cell. In some embodiments, the methods further comprise the step of using the methane or ethanol in a combustion unit.

In some embodiments, the present invention provides methods for reducing carbon dioxide emissions comprising: a) providing a biomass and a population of at least one genus of a hyperthermophilic organism; b) anaerobically degrading said biomass in the presence of said population of at least one genus of a hyperthermophilic organism to produce substrates for energy production; and c) producing energy from said substrates, wherein carbon dioxide emissions are reduced as compared to aerobic degradation of said biomass materials. In further embodiments, the present invention provides methods for generating carbon credits comprising: a) providing a biomass and a population of at least one genus of a hyperthermophilic organism; b) anaerobically degrading said biomass in the presence of said population of at least one genus of a hyperthermophilic organism to produce substrates for energy production, and c) producing energy from said substrates under conditions such that carbon credits are generated.

In further embodiments, the present invention provides processes comprising: providing organic matter and a population of at least one genus of a hyperthermophilic organism; degrading said organic matter by fermentation or by anaerobic or aerobic respiration in the presence of said population of at least one genus of a hyperthermophilic organism under conditions such that acetate is produced; and treating said acetate to produce an energy substrate. In some embodiments, the step of treating said acetate to produce an energy substrate comprises contacting said acetate with methane producing microorganisms to produce methane. In some embodiments, the step of treating said acetate to produce an energy substrate comprises culturing algae in the presence of said acetate to produce fatty acids. In some embodiments, the hyperthermophilic organisms are anaerobic hyperthermophilic organisms. In some embodiments, the anaerobic hyperthermophilic organisms are selected from the group consisting of the genera *Pyrococcus, Thermococcus, Acidianus, Palaeococcus, Thermoplasma, Pyrobaculum, Pyrolobus, Pyrodictium, Methanothermus, Methanopyrus, Fervidobacterium* and *Thermotoga*, and combinations thereof. In some embodiments, hyperthermophilic organisms are aerobic hyperthermophilic organisms. In some embodiments, the aerobic hyperthermophilic organisms are selected from the group consisting of *Aeropyrum pernix, Sulfolobus solfataricus, Metallosphaera sedula, Sulfolobus tokodaii, Thermoplasma acidophilum* and *Thermoplasma volcanium*, and combinations thereof. In some embodiments, the organic matter is selected from the group consisting of sewage, agricultural waste products, brewery grain by-products, food waste, organic industry waste, forestry waste, crops, grass, seaweed, especially brown algae, plankton, algae, fish, fish waste, corn potato waste, sugar cane waste, sugar beet waste, straw, paper waste, chicken manure, cow manure, hog manure, switchgrass and combinations thereof. In some embodiments, the biomass has been previously fermented. In some embodiments, the biomass has been previously fermented in an anaerobic system in the presence of methanogenic microorganisms.

In some embodiments, the present invention provides systems comprising: a first bioreactor containing biomass and a population of at least one genus of hyperthermophilic organisms; and a second bioreactor containing methanogenic bacteria, wherein fermented biomass from said first bioreactor is transported to said second bioreactor. In some embodiments, the first bioreactor and said second bioreactor are in fluid communication.

In some embodiments, the present invention provides systems comprising: a bioreactor containing biomass and a population of at least one genus of hyperthermophilic organisms; and a culture system comprising algae, wherein said bioreactor and said culture system are in fluid communication. In some embodiments, the bioreactor and said culture system are in fluid communication.

In some embodiments, the present invention provides processes comprising providing a biomass and a population of at least one genus of a hyperthermophilic organism; fermenting said biomass in the presence of said population of at least one genus of a hyperthermophilic organism under conditions such that acetate is produced; and introducing said acetate into a bioreactor comprising methanogenic microorganisms under conditions such that methane gas is produced.

In some embodiments, the present invention provides processes comprising providing a biomass, a first bioreactor and a second bioreactor; fermenting said biomass in said first bioreactor with methanogenic microorganisms to produce methane and a first fermented biomass; introducing said fermented biomass into said second bioreactor in the presence of a population of at least one genus of hyperthermophilic organisms; fermenting said first fermented biomass in said second bioreactor to produce acetate and a second fermented biomass; and introducing said acetate into said first bioreactor under conditions such that said acetate is converted into methane.

In some embodiments, the present invention provides processes comprising: providing a biomass and a population of at least one genus of a hyperthermophilic organism; culturing said population of at least one genus of a hyperthermophilic organism under anaerobic conditions on said biomass substrate so that said population of at least one genus of a hyperthermophilic organism reaches and maintains a stationary phase; maintaining said population of at least one genus of a hyperthermophilic organism in a predominantly stationary phase; and utilizing heat generated by said culture; and removing an energy substrate from said culture. In some embodiments, the energy substrate is hydrogen. In some embodiments, the energy substrate is ethanol. In some embodiments, the energy substrate is acetate. In some embodiments, the population of at least one genus of a hyperthermophilic organism comprises a population from the genus *Thermatoga*. In some embodiments, the culturing is performed in a continuous bioreactor.

In some embodiments, the present invention provides systems comprising: a continuous bioreactor comprising a biomass and a population of at least one genus of a hyperthermophilic organism wherein said population of at least one genus of a hyperthermophilic organism is maintained in said bioreactor at a stationary phase under anaerobic conditions; wherein said bioreactor has a headspace therein and further comprises a fitting contiguous with the headspace so that $H_2$ can be removed from said headspace via said fitting; and a heat energy transfer system.

In some embodiments, the present invention provides processes comprising: providing a biomass and a population of at least one genus of a hyperthermophilic organism; culturing said population of at least one genus of a hyperthermophilic organism under anaerobic conditions on said biomass substrate so that said population of at least one genus of a hyperthermophilic organism reaches and maintains a stationary phase; maintaining said population of at least one genus of a hyperthermophilic organism in a predominantly stationary phase; and removing an energy substrate from said culture.

In some embodiments, the present invention provides processes comprising: providing a first biomass, a population of at least one genus of a hyperthermophilic organism, and a reducing agent; culturing said population of at least one genus of a hyperthermophilic organism under anaerobic conditions on said biomass substrate in the presence of said reducing agent until the redox potential of the culture is less than about −125 mV, preferably less than about −500 mV; and adding a second biomass to said culture, wherein said second biomass has not been substantially deoxygenated and the redox potential of the culture is sufficient to reduce oxygen in said biomass.

In some embodiments, the present invention provides processes comprising: providing a biomass that contains a human pathogen and a population of at least one genus of a hyperthermophilic organism; culturing said population of at least one genus of a hyperthermophilic organism under anaerobic conditions on said biomass at a temperature of 80° C. or higher; maintaining said culture at temperature of 80° C. or higher so that said pathogens are destroyed to provide a decontaminated biomass residue; and processing said decontaminated biomass residue. In some embodiments, the decontaminated biomass residue is processed for use as fertilizer. In some embodiments, the heat generated by said culture is used to heat a liquid external to said culture.

In some embodiments, the present invention provides process comprising providing a biomass and a population of at least one genus of a hyperthermophilic organism; culturing said population of at least one genus of a hyperthermophilic organism under anaerobic conditions on said biomass substrate to produce $H_2$; and combining said $H_2$ with methane to provide a combustible gas. In some embodiments, the culturing also produces $CO_2$ and said combustible gas comprises $CO_2$ in addition to said $H_2$ and methane. In some embodiments, the processes further comprise utilizing heat generated by said culture. In some embodiments, the processes further comprise removing an energy substrate from said culture.

In some embodiments, the present invention provides processes comprising providing organic matter and populations of a first and second hyperthermophilic organisms; in a first stage, degrading said organic matter by fermentation or by anaerobic or aerobic respiration in the presence of said population of said first hyperthermophilic organism to produce hydrogen and acetate; and in a second stage, degrading the organic material from the first stage with said second hyperthermophilic organism to produce hydrogen and acetate. In some embodiments, the first hyperthermophilic organism is *Pyrococcus furiosus* and said second microorganism is *Thermatoga maritima*. In some embodiments, the processes further comprise the step of using said acetate as a substrate produce an energy substrate. In some embodiments, the step of treating said acetate to produce an energy substrate comprises contacting said acetate with methane producing microorganisms to produce methane.

In some embodiments, the present invention provides a system comprising a first bioreactor containing biomass and a population of a first hyperthermophilic organism; and a second bioreactor containing a population of a second hyperthermophilic organisms in fluid communication with said first bioreactor.

In some embodiments, the present invention provides a system comprising a first bioreactor containing biomass and a population of a first hyperthermophilic organism; and a second bioreactor containing a population of a second hyperthermophilic organisms in fluid communication with said first bioreactor; and a third bioreactor containing methanogenic bacteria, in fluid communication with said second bioreactor; wherein said biomass is degraded in the said first bioreactor, transported to said second bioreactor for further degradation, and then transported to said third bioreactor for conversion of acetate to methane.

In some embodiments, the present invention provides a method comprising a) providing a hydrocarbon composition and a population of at least one genus of a hyperthermophilic organism; and b) treating the hydrocarbon composition in the presence of the population of at least one genus of a hyperthermophilic organism under conditions such that degradation products are produced. In some embodiments, the hyperthermophilic organisms are selected from the group consisting of the archaeal genera *Pyrococcus, Thermococcus, Palaeococcus, Acidianus, Pyrobaculum, Pyrolobus, Pyrodictium, Methanopyrus, Methanothermus, Methanobacterium*, hyperthermophilic Methanococci like *Methanocaldococcus jannaschii, Archaeoglobus*, and of the bacterial genera *Thermosipho, Thermotoga, Fervidobacterium, Thermodesulfobacterium* and combinations thereof. In some embodiments, the hydrocarbon composition is selected from the group consisting of produced water from oil wells, oil sand, oil shale, oil waste water, coal waste water, and combinations thereof. In some embodiments, the hydrocarbon composition is supplemented with a biomass component and/or a cell culture media component selected from the group consisting of a mineral source, vitamins, amino acids, an energy source, and a microorganism extract. In some embodiments, the degradation products are selected from the group consisting of hydrogen, methane and ethanol. In some embodiments, the methods further comprise the step of converting the degradation products into energy.

In some embodiments, the present invention provides a method of generating oil or energy substrates comprising delivering a composition comprising hyperthermophilic organisms to an oil bearing formation via an oil well. In some embodiments, the composition comprising hyperthermophilic organisms further comprises a component selected from the group consisting of energy substrate(s), mineral, salts, vitamins, amino acids, and/or microorganism extracts and combinations thereof. In some embodiments, the method further comprises delivering a biomass to the oil bearing formation. In some embodiments, the biomass is preferably selected from the group consisting of sewage, agricultural waste products, brewery grain by-products, food waste, organic industry waste, whey, forestry waste, crops, grass, seaweed, plankton, algae, fish, fish waste, newsprint and combinations thereof. In some embodiments, the hyperthermophilic organisms produce an energy substrate selected from the group consisting of hydrogen, methane and ethanol. In some embodiments, the methods further comprise the step of converting the energy substrates into energy.

In some embodiments, the present invention provides novel *Thermatoga* strains MH-1 (deposited Aug. 31, 2009 with the Deutsche Sammlung von Mikorganismem and Zellkulturen GmBH (DSMZ); Accession No. DSM 22925) and MH-2 (deposited with DSMZ Aug. 31, 2009; Accession No. DSM 22926). It will be recognized that microorganisms having the characteristics of these deposited microorganisms may be utilized in the processes described above. In some embodiments, the present invention provides for the use of microorganisms having the characteristics of MH-1 or MH-2 to treat or process a biomass. In some embodiments, the microorganisms are used to produce degradation products from a biomass, wherein said degradation products are selected from the group consisting of acetate, $H_2$, and ethanol. In some embodiments, the microorganisms are used to pretreat a biomass to produce degradation products that are subsequently utilized in a second culture process. In some embodiments, the present invention provides processes comprising providing a biomass and a hyperthermophilic microorganism; and degrading said biomass in the presence of a cell density of said microorganism of greater than $10^9$ cell/ml under conditions such that degradation products are produced.

In some embodiments, the present invention provides methods comprising a) providing a biomass and a hyperthermophilic microorganism; and b) degrading said biomass in the presence of a cell density of said microorganism of greater than $10^9$ under conditions such that degradation products are produced. In some embodiments, said hyperthermophilic organisms are anaerobic hyperthermophilic organisms. In some embodiments, the microorganism is preferable selected from MH-1 and MH-2. In some embodiments, the biomass is selected from the group consisting of sewage, agricultural waste products, straw, corn stover, brewery grain by-products, food waste, organic industry waste, forestry waste, crops, grass, seaweed, plankton, algae, fish, fish waste, and combinations thereof. In some embodiments, the degradation products are selected from the group consisting of hydrogen, acetate, methane and ethanol. In some embodiments, the methods further comprise the step of converting said degradation products into energy.

In some embodiments, the present invention provides a process comprising: treating a biomass with a hyperthermophillic organism selected from the group consisting of microorganisms having the characteristics of MH-1 (Accession No. DSM 22925) and MH-2 (Accession No. DSM 22926) under conditions such that at least one degradation product is produced. In some embodiments, the processes further comprise the step of separating said at least one degradation from said biomass. In some embodiments, the processes further comprise the step of converting said degradation product into heat or electricity. In some embodiments, the biomass is selected from the group consisting of sewage, agricultural waste products, straw, corn stover, brewery grain by-products, food waste, organic industry waste, forestry waste, crops, grass, seaweed, plankton, algae, fish, fish waste, and combinations thereof. In some embodiments, the biomass is preferably seaweed. In some embodiments, the at least one degradation product are selected from the group consisting of hydrogen, acetate, methane and ethanol and combinations thereof. In some embodiments, the microorganism is MH-1 (Accession No. DSM 22925) and said biomass is degraded in the presence of a cell density of said microorganism of greater than $10^9$. In some embodiments, the degradation product is acetate and further comprising the step of feeding said acetate to methanogenic bacteria under conditions such that said acetate is converted to methane. In some embodiments, the methods further comprise the step of feeding said at least one degradation product to a culture system comprising algae under conditions such that the growth of said algae is enhanced. In some embodiments, the degradation product is acetate. In some embodiments, the methods further comprise the step of producing fatty acids from said algae. In some embodiments, the microorganism is MH-2 (Accession No. DSM 22926) and said biomass is degraded at a salt concentration of less than about 0.2%, 0.1% or 0.05%. In some embodiment, said conditions comprise maintaining said microorganism in a stationary phase.

In some embodiments, the present invention provides processes comprising providing organic matter and a population of at least one genus of a hyperthermophilic organism; degrading said organic matter by fermentation or by anaerobic or aerobic respiration in the presence of said population of at least one genus of a hyperthermophilic organism under conditions such that at least one degradation product is produced; and contacting said at least one degradation product with a second organism to produce an energy substrate. In some embodiments, the at least one degradation product is acetate and said contacting step comprises contacting said acetate with methane producing microorganisms to produce methane. In some embodiments, the contacting step comprises culturing algae in the presence of said at least one degradation product to produce fatty acids. In some embodiments, the hyperthermophilic organisms are anaerobic hyperthermophilic organisms. In some embodiments, the anaerobic hyperthermophilic organisms are selected from the group consisting of the genera *Pyrococcus, Thermococcus, Acidianus, Palaeococcus, Thermoplasma, Pyrobaculum, Pyrolobus, Pyrodictium, Methanotehrmus, Methanopyrus,* and *Fervidobacterium Thermotoga*, and combinations thereof. In some embodiments, the microorganisms preferably have the characteristics of MH-1 (Accession No. DSM 22925) or MH-2 (Accession No. DSM 22926). In some embodiments, the organic matter is selected from the group consisting of sewage, agricultural waste products, brewery grain by-products, food waste, organic industry waste, forestry waste, crops, grass, seaweed, plankton, algae, fish, fish waste, corn potato waste, sugar cane waste, sugar beet waste, straw, paper waste, chicken manure, cow manure, hog manure, switchgrass and combinations thereof. In some embodiments, the biomass has been previously fermented. In some embodiments, the biomass has been previously fermented in an anaerobic system in the presence of methanogenic microorganisms. In some embodiments, the biomass is in a liquid medium with a salt concentration of less than about 0.2%.

In some embodiments, the present invention provides processes comprising treating a biomass with a hyperthermophillic organism under conditions such that at least one degradation product is produced, wherein the biomass is provided in a liquid medium with a salt concentration of less than 0.2%.

In some embodiments, the present invention provides a process comprising providing a biomass and a population of at least one genus of a hyperthermophilic organism; culturing said population of at least one genus of a hyperthermophilic organism under anaerobic conditions on said biomass substrate to produce $H_2$ and/or $CO_2$; and adding said $H_2$ and/or $CO_2$ to a biogas reactor to increase production of methane.

DEFINITIONS

Figure 1:
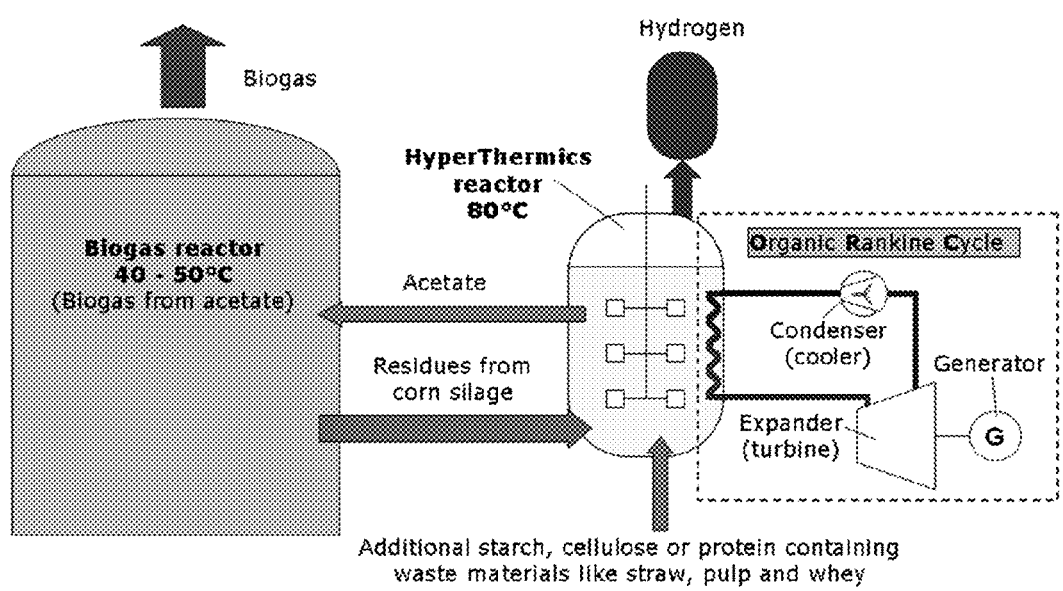
FIG. 1 depicts a bioreactor of the present invention coupled to waste material in the efflux of a Biogas reactor and to an Organic Rankine Cycle system

As used herein, the term "biomass" refers to biological material which can be used as fuel or for industrial production. Most commonly, biomass refers to plant matter grown for use as biofuel, but it also includes plant or animal matter used for production of fibers, chemicals or heat. Biomass may also include biodegradable wastes that can be used as fuel. It is usually measured by dry weight. The term biomass is useful for plants, where some internal structures may not always be considered living tissue, such as the wood (secondary xylem) of a tree. This biomass became produced from plants that convert sunlight into plant material through photosynthesis. Sources of biomass energy lead to agricultural crop residues, energy plantations, and municipal and industrial wastes. The term "biomass," as used herein, excludes components of traditional media used to culture microorganisms, such as purified starch, peptone, yeast extract but includes waste material obtained during industrial processes developed to produce purified starch. According to the invention, biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn steep liquor, grasses, wheat, wheat straw, barley, barley straw, grain residue from barley degradation during brewing of beer, hay, rice straw, switchgrass, waste paper, sugar cane bagasse, sorghum, soy, components obtained from processing of grains, trees, branches, roots, leaves, wood chips, sawdust, shrubs and bushes, soybean hulls, vegetables, fruits, flowers and animal manure. In one embodiment, biomass that is useful for the invention includes biomass that has a relatively high carbohydrate value, is relatively dense, and/or is relatively easy to collect, transport, store and/or handle.

As used herein, the term "biomass by-products" refers to biomass materials that are produced from the processing of biomass.

As used herein, the term "bioreactor" refers to an enclosed or isolated system for containment of a microorganism and a biomass material. The "bioreactor" may preferably be configured for anaerobic growth of the microorganism.

As used herein, the term "hyperthermophilic organism" means an organism which grows optimally at temperatures above 80° C.

As used herein, the terms "degrade" and "degradation" refer to the process of reducing the complexity of a substrate, such as a biomass substrate, by a biochemical process, preferably facilitated by microorganisms (i.e., biological degradation). Degradation results in the formation of simpler compounds such as methane, ethanol, hydrogen, and other relatively simple organic compounds (i.e., degradation products) from complex compounds. The term "degradation" encompasses anaerobic and aerobic processes, including fermentation processes.

DETAILED DESCRIPTION OF THE INVENTION

The present invention relates to the field of biomass degradation with hyperthermophilic organisms, and in particular to the use of hyperthermophilic degradation to produce heat, ethanol, hydrogen and other energy substrates from a biomass. For convenience, the description of the invention is provided in the following section: A. Hyperthermophilic organisms; B. Biomass; C. Degradation and energy production; D. Treatment of hydrocarbon sources; E. Utilization of acetate; and F. Carbon credit generation.

A. Hyperthermophilic Organisms

The present invention comtemplates the use of hyperthermophilic organism for fermenting biomass. Thermophilic bacteria are organisms which are capable of growth at elevated temperatures. Unlike the mesophiles, which grow best at temperatures in the range of 25-40 C, or psychrophiles, which grow best at temperatures in the range of 15-20 C, thermophiles grow best at temperatures greater than 50 C. Indeed, some thermophiles grow best at 65-75 C, and hyperthermophiles grow at temperatures higher than 80 C up to 113 C. (See e.g., J. G. Black, *Microbiology Principles and Applications*, 2d edition, Prentice Hall, New Jersey, [1993] p. 145-146; Dworkin, M., Falkow, S., Rosenberg, E, Schleifer, K-H., Stackebarndt E. (eds) The prokaryotes, third edition, volume 3, p. 3-28296 and p. 797-814 and p. 899-924; Madigan M., Martinko, J. Brock Biology of Microorganisms, eleventh edition, p. 430-441 and 414-415).

The thermophilic bacteria encompass a wide variety of genera and species. There are thermophilic representatives included within the phototrophic bacteria (i.e., the purple bacteria, green bacteria, and cyanobacteria), bacteria (i.e., *Bacillus, Clostridium, Thiobacillus, Desulfotomaculum, Thermus*, Lactic acid bacteria, *Actinomycetes, Spirochetes*, and numerous other genera). Many hyperthermophiles are archaea (i.e., *Pyrococcus, Thermococcus, Thermotoga, Sulfolobus*, and some methanogens). There are aerobic as well as anaerobic thermophilic organisms. Thus, the environments in which thermophiles may be isolated vary greatly, although all of these organisms are isolated from areas associated with high temperatures. Natural geothermal habitats have a worldwide distribution and are primarily associated with tectonically active zones where major movements of the earth's crust occur. Thermophilic bacteria have been isolated from all of the various geothermal habitats, including boiling springs with neutral pH ranges, sulfur-rich acidic springs, and deep-sea vents. In general, the organisms are optimally adapted to the temperatures at which they are living in these geothemal habitats (T. D. Brock, "Introduction: An overview of the thermophiles," in T. D. Brock (ed.), *Thermophiles: General, Molecular and Applied Microbiology*, John Wiley & Sons, New York [1986], pp. 1-16; Madigan M., Martinko, J. Brock Biology of Microorganisms, eleventh edition, p. 442-446 and p. 299-328). Basic, as well as applied research on thermophiles has provided some insight into the physiology of these organisms, as well as promise for use of these organisms in industry and biotechnology.

The present invention is not limited to the use of any particular hyperthermophilic organism. In some embodiments, mixtures of hyperthermophilic organisms are utilized. In some embodiments, the hyperthermophiles are from the archaeal order *Thermococcales*, including but not limited to hyperthermophiles of the genera *Pyrococcus, Thermococcus*, and *Palaeococcus*. Examples of particular organisms within these genera include, but are not limited to, *Pyrococcus furiosus, Thermococcus barophilus, T. aggregans, T. aegaeicus, T. litoralis, T. alcaliphilus, T. sibiricus, T. atlanticus, T. siculi, T. pacificus, T. waiotapuensis, T. zilligi, T. guaymasensis, T. fumicolans, T. gorgonarius, T. celer, T. barossii, T. hydrothermalis, T. acidaminovorans, T. profundus, T. stetteri, T. kodakaraensis, T. peptonophilis*. In some embodiments, aerobic hyperthermophilic organisms such as *Aeropyrum pernix, Sulfolobus solfataricus, Metallosphaera sedula, Sulfolobus tokadaii, Sulfolobus shibatae, Thermoplasma acidophilum* and *Thermoplasma volcanium* are utilized. While in other embodiments, anaerobic or facultative aerobic organisms such as *Pyrobaculum calidifontis* and *Pyrobaculum oguniense* are utilized. Other useful archaeal organisms include, but are not limited to, *Sulfolobus acidocaldarius* and *Acidianus ambivalens*. In some embodiments, the hyperthermophilic organisms are bacteria, such as *Thermus aquaticus, Thermus thermophilus, Thermus flavus, Thermus ruber, Bacillus caldotenax, Geobacillus stearothermophilus, Anaerocellum thermophilus, Thermoactinomyces vulgaris*, and members of the order Thermotogales, including, but not limited to *Thermotoga elfeii, Thermotoga hypogea, Thermotoga maritima, Thermotoga neapolitana, Thermotoga subterranean, Thermotoga thermarum, Petrotoga miotherma, Petrotoga mobilis, Thermosipho africanus, Thermosipho melanesiensis, Fervidobacterium islandicum, Fervidobacterium nodosum, Fervidobacterium pennavorans, Fervidobacterium gondwanense, Geotoga petraea, Geotoga subterranea*. In some preferred embodiments, the microorganism preferably has the characteristics of *Thermatoga* strain MH-1, Accession No. DSM 22925 or *Thermatoga* strain MH-2, Accession No. DSM 22926.

In some embodiments, hyperthermophilic strains of the above organisms suitable for fermenting biomass will be selected by screening and selecting for suitable strains. In still further embodiments, suitable strains will be genetically modified to include desirable metabolic enzymes, including, but not limited to hydrolytic enzymes, proteases, alcohol dehydrogenase, and pyruvate decarboxylase. See, e.g., (Bra/u, B., and H. Sahm [1986] Arch. Microbiol. 146:105-110; Bra/u, B. and H. Sahm [1986] Arch. Microbiol. 144:296-301; Conway, T., Y. A. Osman, J. I. Konnan, E. M. Hoffmann, and L. O. Ingram [1987] J. Bacteriol. 169:949-954; Conway, T., G. W. Sewell, Y. A. Osman, and L. O. Ingram [1987] J. Bacteriol. 169:2591-2597; Neale, A. D., R. K. Scopes, R. E. H. Wettenhall, and N. J. Hoogenraad [1987] Nucleic Acid. Res. 15:1753-1761; Ingram, L. O., and T. Conway [1988] Appl. Environ. Microbiol. 54:397-404; Ingram, L. O., T. Conway, D. P. Clark, G. W. Sewell, and J. F. Preston [1987] Appl. Environ. Microbiol. 53:2420-2425). In some embodiments, a PET operon is introduced into the hyperthermophile. See U.S. Pat. No. 5,000,000, incorporated herein by reference in its entirety.

In some embodiments, hyperthermophiles that produce ethanol via degradation are selected. In some embodiments, such hyperthermophiles are selected in media containing progressively higher amounts of ethanol to select for strains with increased ethanol tolerance. Accordingly, some embodiments of the present invention provide hyperthermophiles with increased ethanol tolerance or increased ability to produce ethanol. In some preferred embodiments, the hyperthermophiles utilize lignocellulosic biomass. In further preferred embodiments, the hyperthermophile utilize glucose, xylose, arabinose, galactose, and mannose.

B. Biomass and Organic Matter

The present invention contemplates the degradation of biomass with hyperthermophilic organisms. The present invention is not limited to the use of any particular biomass or organic matter. Suitable biomass and organic matter includes, but is not limited to, sewage, agricultural waste products, brewery grain by-products, food waste, organic industry waste, forestry waste, crops, grass, seaweed, plankton, algae, fish, fish waste, corn potato waste, sugar cane waste, sugar beet waste, straw, paper waste, chicken manure, cow manure, hog manure, switchgrass and combinations thereof. In some embodiments, the biomass is harvested particularly for use in hyperthermophilic degradation processes, while in other embodiments waste or by-products materials from a pre-existing industry are utilized.

In some preferred embodiments, the biomass is lignocellulosic. In some embodiments, the biomass is pretreated with cellulases or other enzymes to digest the cellulose. In some embodiments, the biomass is pretreated by heating in the presence of a mineral acid or base catalyst to completely or partially hydrolyze hemicellulose, de-crystallize cellulose, and remove lignin. This allows cellulose enzymes to access the cellulose.

In still other preferred embodiments, the biomass is supplemented with minerals, energy sources or other organic substances. Examples of minerals include, but are not limited to, those found in seawater such as NaCl, $MgSO_4 \times 7H_2O$, $MgCl_2 \times 6H_2O$, $CaCl_2 \times 2H_2O$, KCl, NaBr, $H_3BO_3$, $SrCl_2 \times 6H_2O$ and KI and other minerals such as $MnSO_4 \times H_2O$, $FeSO_4 \times 7H_2O$, $CoSO_4 \times 7H_2O$, $ZnSO_4 \times 7H_2O$, $CuSO_4 \times 5H_2O$, $KAl(SO_4)_2 \times 12H_2O$, $Na_2MoO_4 \times 2H_2O$, $(NH_4)_2Ni(SO_4)_2 \times 6H_2O$, $Na_2WO_4 \times 2H_2O$ and $Na_2SeO_4$.

Examples of energy sources and other substrates include, but are not limited to, purified sucrose, fructose, glucose, starch, peptone, yeast extract, amino acids, nucleotides, nucleosides, and other components commonly included in cell culture media.

In other embodiments, the biomass that is utilized has been previously fermented by another process. Surprisingly, it has been found that hyperthermophilic organisms are capable of growing on biomass that has been previously fermented by methanogenic microorganisms.

In some embodiments, biomass that contains or is suspected of containing human pathogens is treated by the hyperthermophilic process to destroy the pathogenic organisms. In some preferred embodiments, the biomass is heated to about 80° C. to 120° C., preferably to about 100° C. to 120° C., for a time period sufficient to render pathogens harmless. In this manner, waste such a human sewage may be treated so that it can be further processed to provide a safe fertilizer, soil amendment of fill material in addition to other uses.

In some preferred embodiments, the biomass is an algae, most preferably a marine algae (seaweed). In some embodiments, marine algae is added to another biomass material to stimulate hydrogen and/or acetate production. In some embodiments, the biomass substrate comprises a first biomass material that is not marine algae and marine algae in a concentration of about 0.01% to about 50%, weight/weight (w/w), preferably 0.1% to about 50% w/w, about 0.1% to about 20% w/w, about 0.1% to about 10% w/w, about 0.1% to about 5% w/w, or about preferably 1.0% to about 50% w/w, about 1.0% to about 20% w/w, about 1.0% to about 10% w/w, or about 1.0% to about 5% w/w. The present invention contemplates the use of a wide variety of seaweeds, including, but not limited to, marine algaes such as cyanobacteria (blue-green algae), green algae (division Chlorophyta), brown algae (Phaeophyceae, division Phaeophyta), and red algae (division Rhodophyta). In some embodiments, the brown algae is a kelp, for example, a member of genus *Laminaria* (*Laminaria* sp), such as *Laminaria hyperborea, Laminaria digitata, Laminaria abyssalis, Laminaria agardhii, Laminaria angustata, Laminaria appressirhiza, Laminaria brasiliensis, Laminaria brongardiana, Laminaria bulbosa, Laminaria bullata, Laminaria complanata, Laminaria dentigera, Laminaria diabolica, Laminaria ephemera, Laminaria farlowii, Laminaria inclinatorhiza, Laminaria multiplicata, Laminaria ochroleuca, Laminaria pallid, Laminaria platymeris, Laminaria rodriguezii, Laminaria ruprechtii, Laminaria sachalinensis, Laminaria setchellii, Laminaria sinclairii, Laminaria solidugula* and *Laminaria yezoensis* or a member of the genus *Saccharina* (*Saccharina* sp.), such as *Saccharina angustata, Saccharina bongardiana, Saccharina cichorioides, Saccharina coriacea, Saccharina crassifolia, Saccharina dentigera, Saccharina groenlandica, Saccharina gurjanovae, Saccharina gyrate, Saccharina japonica, Saccharina kurilensis, Saccharina latissima, Saccharina longicruris, Saccharina longipedales, Saccharina longissima, Saccharina ochotensis, Saccharina religiosa, Saccharina sculpera, Saccharina sessilis*, and *Saccharina yendoana*. In some embodiments, the brown algae if from one of the following following genera: *Fucus, Sargassum*, and *Ectocarpus*.

C. Degradation and Energy Production

In preferred embodiments of the present invention, one or more populations of hyperthermophilic organisms are utilized to degrade biomass. In some embodiments, the biomass is transferred to a vessel such as a bioreactor and inoculated with one or more strains of hyperthermophilic organisms. In some embodiments, the environment of the vessel is maintained at a temperature, pressure, redox potential, and pH sufficient to allow the strain(s) to metabolize the feedstock. In some preferred embodiments, the environment has no added sulfur or inorganic sulfide salts or is treated to remove or neutralize such compounds. In other, embodiments, reducing agents, including sulfur containing compounds, are added to the initial culture so that the redox potential of the culture is lowered. In some preferred embodiments, the environment is maintained at a temperature above 45° C. In still further embodiments, the environment is maintained at between 55 and 90° C. In still further embodiments, the culture is maintained at from about 80° C. to about 110° C. depending on the hyperthermophilic organism utilized. In some preferred embodiments, sugars, starches, xylans, celluloses, oils, petroleums, bitumens, amino acids, long-chain fatty acids, proteins, or combinations thereof, are added to the biomass. In some embodiments, water is added to the biomass to form an at least a partially aqueous medium. In some embodiments, the aqueous medium has a dissolved oxygen gas concentration of between about 0.2 mg/liter and 2.8 mg/liter. In some embodiments, the environment is maintained at a pH of between approximately 4 and 10. In some embodiments, the environment is preconditioned with an inert gas selected from a group consisting of nitrogen, carbon dioxide, helium, neon, argon, krypton, xenon, and combinations thereof. While in other embodiments, oxygen is added to the environment to support aerobic degradation.

In other embodiments, the culture is maintained under anaerobic conditions. In some embodiments, the redox potential of the culture is maintained at from about −125 mV to −850 mV, and preferably below about −500 mV. Surprisingly, in some embodiments, the redox potential is maintained at a level so that when a biomass substrate containing oxygen is added to an anaerobic culture, any oxygen in the biomass is reduced thus removing the oxygen from the culture so that anaerobic conditions are maintained.

In some embodiments, where lignocellulosic materials are utilized, the cellulose is pre-treated as described above. The pre-treated cellulose is enzymatically hydrolyzed either prior to degradation in sequential saccharification and degradation or by adding the cellulose and hyperthermophile inoculum together for simultaneous saccharification and degradation.

It is contemplated that degradation of the biomass will both directly produce energy in the form of heat (i.e., the culture is exothermic or heat-generating) as well as produce products that can be used in subsequent processes, including the production of energy. In some embodiments, hydrogen, methane, and ethanol are produced by the degradation and utilized for energy production. In preferred embodiments, these products are removed from the vessel. It is contemplated that removal of these materials in the gas phase will be facilitated by the high temperature in the culture vessel. These products may be converted into energy by standard processes including combustion and/or formation of steam to drive steam turbines or generators. In some embodiments, the hydrogen is utilized in fuel cells. In some embodiments, proteins, acids and glycerol are formed which can be purified for other uses or, for example, used as animal feeds.

In some embodiments, the culture is maintained so as to maximize hydrogen production. In some embodiments, the culture is maintained under anaerobic conditions and the population of microorganisms is maintained in the stationary phase. Stationary phase conditions represent a growth state in which, after the logarithmic growth phase, the rate of cell division and the one of cell death are in equilibrium, thus a constant concentration of microorganisms is maintained in the vessel.

In some embodiments, the degradation products are removed from the vessel. It is contemplated that the high temperatures at which the degradation can be conducted facilitate removal of valuable degradation products from the vessel in the gas phase. In some embodiments, methane, hydrogen and/or ethanol are removed from the vessel. In some embodiments, these materials are moved from the vessel via a system of pipes so that the product can be used to generate power or electricity. For example, in some embodiments, methane or ethanol are used in a combustion unit to generate power or electricity. In some embodiments, steam power is generated via a steam turbine or generator. In some embodiments, the products are packages for use. For example, the ethanol, methane or hydrogen can be packaged in tanks or tankers and transported to a site remote from the fermenting vessel. In other embodiments, the products are fed into a pipeline system.

In still other embodiments, heat generated in the vessel is utilized. In some embodiments, the heat generated is utilized in radiant system where a liquid is heated and then circulated via pipes or tubes in an area requiring heating. In some embodiments, the heat is utilized in a heat pump system. In still other embodiments, the heat is utilized to produce electricity via a thermocouple. In some embodiments, the electricity produced is used to generate hydrogen via an electrolysis reaction.

In other preferred embodiments, the excess heat generated by the fermentation process is used to generate electricity in an Organic Rankine Cycle (ORC) (see FIG. 1). A Rankine cycle is a thermodynamic cycle which converts heat into work. The heat is supplied externally to a closed loop, which usually uses water as the working fluid to drive a turbine coupled to the system. Conventional Rankine cycle processes generate about 80% of all electric power used in America and throughout the world, including virtually all solar thermal, biomass, coal and nuclear power plants. The organic Rankine cycle (ORC) uses an organic fluid such as pentane or butane in place of water and steam. This allows use of lower-temperature heat sources, which typically operate at around 70-90° C. An example of an ORC system coupled to a heat-producing bioreactor of the present invention is depicted in FIG. 1. Heat from the bioreactor, which runs at approximately 80° C., is used to heat an organic solvent such as perfluor pentane in a closed loop. The heated solvent expands through a turbine and generates electricity via the generator. The solvent cools and is passed though a condenser.

Figure 4:
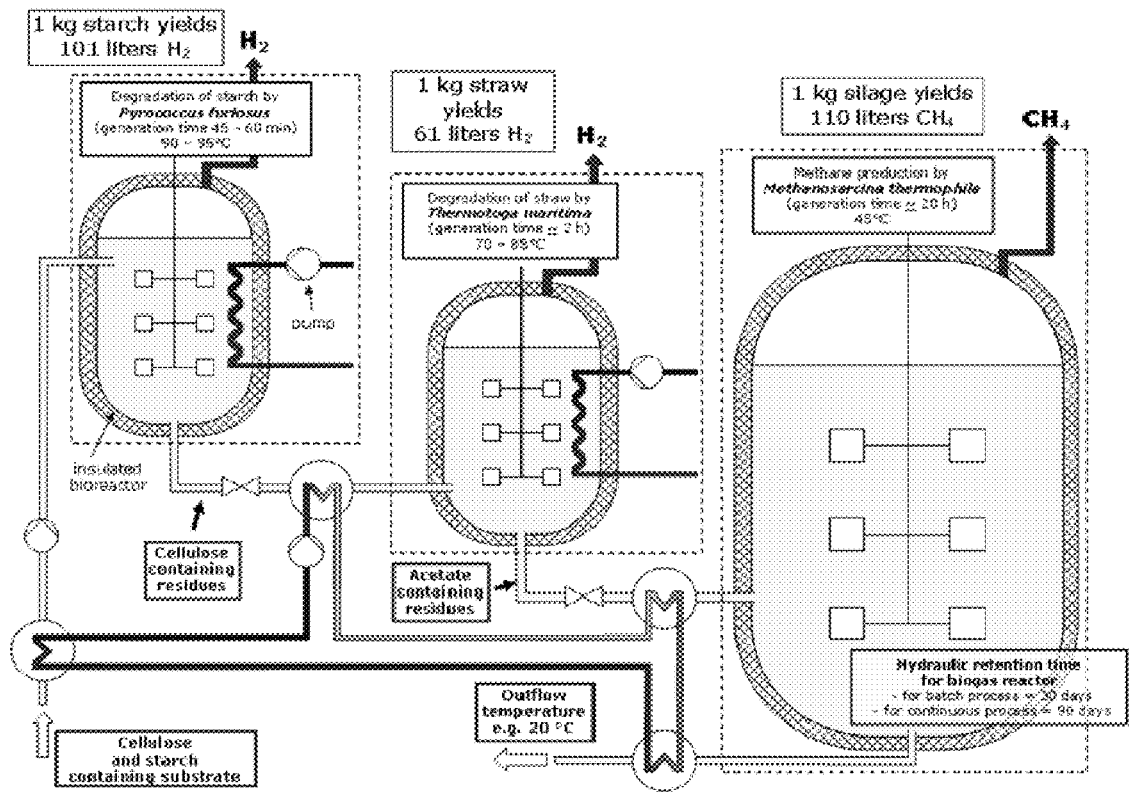
FIG. 4 provides a schematic depiction of a two-stage hydrogen production process coupled to a methane production process.

In other preferred embodiments, the present invention provides a process in which biomass is treated in two or more stages with hyperthermophilic organisms. In some embodiments, the process comprise a first stage where a first hyperthermophilic organism is used to treat a biomass substrate, and a second stage where a second hyperthermophilic organism is used to treat the material produced from the first stage. Additional hyperthermophilic degradation stages can be included. In some embodiments, the first stage utilizes *Pyroccoccus furiosus*, while the second stage utilizes *Thermotoga maritima*. A preferred embodiment is depicted in FIG. 4. In some preferred embodiments, the material produced from the second stage, including acetate, is further utilized as a substrate for methane production as described in more detail below.

In some embodiments, $H_2$ and/or $CO_2$ produced during hyperthermophilic degradation of a biomass are combined with methane from a biogas facility to provide a combustible gas. In some embodiments, $H_2$ and/or $CO_2$ producing during hyperthermophilic degradation of a biomass are added to a biogas reactor to increase production of methane.

The present invention also provides systems, compositions and processes for degrading biomass under improved conditions. In some embodiments, a hyperthermophile strain derived from a marine hyperthermophile is utilized and the biomass is provided in a liquid medium that comprises less than about 0.2% NaCl. In some embodiments, the NaCl concentration ranges from about 0.05% to about 0.2%, preferably about 0.1% to about 0.2%. In some embodiments, the preferred strain is MH-2 (Accession No. DSM 22926). In these embodiments, the biomass is suspended in a liquid medium so that it can be pumped into a bioreactor system. It is contemplated that the lower salt concentration allows use of the residue left after degradation for a wider variety of uses and also results in less corrosion of equipment. Furthermore, the lower salt concentration allows for direct introduction of the degraded biomass containing acetate, or liquid medium containing acetate that is derived from the hyperthermophilic degradation, into a biogas reactor.

In further embodiments, the processes and microorganisms described herein facilitate degradation of biomass using concentrations of hyperthermophilic organisms that have not been previously described. In some embodiments, the concentration of the hyperthermophilic organism in the bioreactor is greater than about $10^9$ cells/ml. In some embodiments, the cell concentration ranges from about $10^9$ cells/ml to about $10^{11}$ cells/ml, preferably from about $10^9$ cells/ml to about $10^{10}$ cells/ml.

In still further embodiments, the present invention provides processes that substantially decrease the hydraulic retention time of a given amount of biomass in a reactor. Hydraulic retention time is a measure of the average length of time that a soluble compound, in this case biomass suspended or mixed in a liquid medium, remains in a constructed reactor and is presented in hours or days. In some embodiments, the hydraulic retention time of biomass material input into a bioreactor in a process of the present invention is less than about 10 hours, preferably less than about 5 hours, more preferably less than about 4 hours, and most preferably less than about 3 or 2 hours. In some embodiments, the hydraulic retention time in a hyperthermophilic degradation process of the present invention is from about 1 to about 10 hours, preferably from about 1 to 5 hours, and most preferably from about 2 to 4 hours.

D. Treatment of Hydrocarbon Sources

In some embodiments, hyperthermophilic organisms are used to treat or process a hydrocarbon composition. Examples of hydrocarbon compositions include, but are not limited to crude oil, produced water from oil wells, produced water from coal bed methane, oil sand, oil shale, oil waste water, coal waste water, and the like.

Produced water is water trapped in underground formations that is brought to the surface along with oil or gas. It is by far the largest volume byproduct or waste stream associated with oil and gas production. Management of produced water presents challenges and costs to operators. According to the American Petroleum Institute (API), about 18 billion barrels (bbl) of produced water was generated by U.S. onshore operations in 1995 (API 2000). Additional large volumes of produced water are generated at U.S. offshore wells and at thousands of wells in other countries. Khatib and Verbeek (2003) estimate that for 1999, an average of 210 million bbl of water was produced each day worldwide. This volume represents about 77 billion bbl of produced water for the entire year.

In subsurface formations, naturally occurring rocks are generally permeated with fluids such as water, oil, or gas (or some combination of these fluids). It is believed that the rock in most oil-bearing formations was completely saturated with water prior to the invasion and trapping of petroleum (Amyx et al. 1960). The less dense hydrocarbons migrated to trap locations, displacing some of the water from the formation in becoming hydrocarbon reservoirs. Thus, reservoir rocks normally contain both petroleum hydrocarbons (liquid and gas) and water. Sources of this water may include flow from above or below the hydrocarbon zone, flow from within the hydrocarbon zone, or flow from injected fluids and additives resulting from production activities. This water is frequently referred to as "connate water" or "formation water" and becomes produced water when the reservoir is produced and these fluids are brought to the surface. Produced water is any water that is present in a reservoir with the hydrocarbon resource and is produced to the surface with the crude oil or natural gas.

When hydrocarbons are produced, they are brought to the surface as a produced fluid mixture. The composition of this produced fluid is dependent on whether crude oil or natural gas is being produced and generally includes a mixture of either liquid or gaseous hydrocarbons, produced water, dissolved or suspended solids, produced solids such as sand or silt, and injected fluids and additives that may have been placed in the formation as a result of exploration and production activities. Production of coal bed methane (CBM) involves removal of formation water so that the natural gas in the coal seams can migrate to the collection wells. This formation water is also referred to as produced water. It shares some of the same properties as produced water from oil or conventional gas production, but may be quite different in composition.

Accordingly, in some embodiments, the present invention further provides methods comprising: a) providing a hydrocarbon composition and a population of at least one genus of a hyperthermophilic organism; and b) treating the hydrocarbon composition in the presence of the population of at least one genus of a hyperthermophilic organism under conditions such that degradation products are produced. In some preferred embodiments, the anaerobic hyperthermophilic organisms are selected from the group consisting of the archaeal genera *Pyrococcus, Thermococcus, Palaeococcus, Acidianus, Pyrobaculum, Pyrolobus, Pyrodictium, Methanopyrus, Methanothermus, Methanobacterium,* hyperthermophilic *Methanococci* like *Methanocaldococcus jannaschii, Archaeoglobus*, and of the bacterial genera *Thermosipho, Thermotoga, Fervidobacterium, Thermodesulfobacterium* and combinations thereof. In some preferred embodiments, the hydrocarbon composition is selected from the group consisting of produced water from oil wells, oil sand, oil shale, oil waste water, coal waste water, and the like, and combinations thereof. In some embodiments, the hydrocarbon composition is supplemented with a biomass component such as those described in detail above and/or a cell culture media component selected from the group consisting of a mineral source, vitamins, amino acids, an energy source, and a microorganism extract. In some further preferred embodiments, the degradation products are selected from the group consisting of hydrogen, methane and ethanol. In some embodiments, the methods further comprise the step of converting the degradation products into energy. In some embodiments, the methods further comprise the step of using the hydrogen in a fuel cell. In some embodiments, the methods further comprise the step of using the methane or ethanol in a combustion unit.

In other embodiments, the present invention provides methods of treating oil wells or oil bearing formations with hyperthermophilic organisms. In these embodiments, a composition comprising active or dormant hyperthermophilic organisms is injected into an oil well or into an oil bearing formation via an oil well, injection well or bore hole. The producer bore hole in an oil well is generally lined in the hydrocarbon bearing stratum with "gravel packs", sand containing filter elements, which serve to trap formation fragments and it has been proposed to include in such gravel packs ceramic particles coated with or impregnated with well treatment chemicals such as scale inhibitors (see EP-A-656459 and WO 96/27070) or bacteria (see WO 99/36667). Likewise treatment of the formation surrounding the producer well bore hole with well treatment chemicals before hydrocarbon production begins has also been proposed, e.g. in GB-A-2290096 and WO 99/54592.

In some preferred embodiments, the anaerobic hyperthermophilic organisms are selected from the group consisting of the genera consisting of the archaeal genera *Pyrococcus, Thermococcus, Palaeococcus, Acidianus, Pyrobaculum, Pyrolobus, Pyrodictium, Methanopyrus, Methanothermus, Methanobacterium,* hyperthermophilic *Methanococci* like *Methanocaldococcus jannaschii, Archaeoglobus*, and of the bacterial genera *Thermosipho, Thermotoga, Fervidobacterium, Thermodesulfobacterium* and combinations thereof. In some embodiments, the composition comprising hyperthermophilic organisms comprises a medium that facilitates growth of the hyperthermophilic organism, including energy substrates and other culture components such as mineral, salts, vitamins, amino acids, and/or microorganism extracts such as yeast extracts. In some embodiments, the compositions comprise a biomass substrate such as those described in detail above. In some embodiments, the composition comprising hyperthermophilic organisms is packaged in a vehicle that allows delivery via an oil well and designed to release its contents at a predetermined location within the well, such as at the site of an oil bearing formation. In some embodiments, the compositions further comprise a matrix for delivery of the hyperthermophilic organisms. Various polymeric, oligomeric, inorganic and other particulate carriers for well treatment chemicals are also known, e.g. ion exchange resin particles (see U.S. Pat. No. 4,787,455), acrylamide polymer particles (see EP-A-193369), gelatin capsules (see U.S. Pat. No. 3,676,363), oligomeric matrices and capsules (see U.S. Pat. Nos. 4,986,353 and 4,986,354), ceramic particles (see WO 99/54592, WO 96/27070 and EP-A-656459), and particles of the well treatment chemical itself (see WO 97/45625). These particles may be adapted for delivery of hyperthermophilic organisms.

In the method of the invention the compositions comprising hyperthermophilic organisms may be placed down hole before and/or after hydrocarbon production (i.e. extraction of oil or gas from the well) has begun. In some embodiments, the bacteria are placed down hole before production has begun, especially in the completion phase of well construction.

The compositions comprising hyperthermophilic organisms may be placed within the bore hole (e.g. in the hydrocarbon bearing strata or in ratholes) or within the surrounding formation (e.g. in fissures or within the rock itself). In the former case, the compositions comprising hyperthermophilic organisms are conveniently impregnated into particles contained within a tubular filter, e.g., a gravel pack or a filter structure as disclosed in EP-A-656459 or WO 96/27070; in the latter case, the compositions comprising hyperthermophilic organisms (optionally impregnated into particles) are preferably positioned by squeezing a liquid composition comprising hyperthermophilic organisms down the bore hole. Preferably, before production begins the compositions comprising hyperthermophilic organisms are placed both within the bore in a filter and within the surrounding formation. The hyperthermophilic organisms are alternatively inoculated into the particles.

Where the hyperthermophilic organisms (typically impregnated into particles) are placed within the surrounding formation, the pressure used should be sufficient to cause the bacteria to penetrate at least 1 m, more preferably at least 1.5 m, still more preferably at least 2 m, into the formation. If desired, the hyperthermophilic organisms may be applied in conjunction with porous particles to achieve a penetration of about 2 m or more into the formation.

Compositions comprising such small, porous particles and bacteria according to the invention, which may be co-blended with nutrients, form a further aspect of the invention.

Particles soaked or loaded (also referred to herein as impregnated) with hyperthermophilic organisms according to the invention advantageously have mode particle sizes (e.g., as measured with a Coulter particle size analyzer) of 1 Am to 5 mm, more preferably 10 Am to 1000 ym, especially 250 to 800/mi. For placement within the formation, the mode particle size is preferably 1 to 50 ym, especially 1 to 20 Am e.g. 1-5 Am. For any particular formation, formation permeability (which correlates to the pore throat sizes in the formation) may readily be determined using rock samples taken during drilling and the optimum impregnated particle size may thus be determined. Since the particles produced as described in EP-B-3905, U.S. Pat. No. 4,530,956 and WO 99/19375 have a very low dispersity (i.e. size variation), a highly uniform deposition and deep penetration into the formation can be achieved. For this reason, the particles preferably have a coefficient of variation (CV) of less than 10%, more preferably less than 5%, still more preferably less than 2 W.

CV is determined in percentage as CV=100×standard deviation mean where mean is the mean particle diameter and standard deviation is the standard deviation in particle size. CV is preferably calculated on the main mode, i.e. by fitting a monomodal distribution curve to the detected particle size distribution. Thus some particles below or above mode size may be discounted in the calculation which may for example be based on about 90% of total particle number (of detectable particles that is). Such a determination of CV is performable on a Coulter LS 130 particle size analyzer. For placement in filters, the impregnated particles preferably have mode particle sizes of 50 to 5000 ym, more especially 50 to 1000 Um, still more preferably 100 to 500 Am. In such filters, the impregnated particles preferably constitute 1 to 99% wt, more preferably 2 to 30% wt, still more preferably 5 to 20% wt of the particulate filter matrix, the remaining matrix comprising particulate oil- and water-insoluble inorganic material, preferably an inorganic oxide such as silica, alumina or alumina-silica. Particularly preferably, the inorganic oxide has a mode particle size which is similar to that of the impregnated polymer particles, e.g. within 20%, more preferably within 10%. As with the in-formation placement, the impregnated particles preferably have low dispersity, e.g. a CV of less than 10%, more preferably less than 5%, still more preferably less than 2 W. The low dispersity serves to hinder clogging of the filters.

The pores of the particles will be large enough to allow the microorganisms to penetrate without difficulties e.g. a pore radius of up to 2-4 ym. The impregnated particles are preferably particles having a pore volume of at least 50%, more preferably at least 70%, e.g up to at least 85%.

The bacterially impregnated polymer particles used according to the invention, e.g. MPP or other step-grown polymer particles are preferably vinyl homo- and copolymers more preferably styrenic homo- and copolymers. Examples of appropriate monomers include vinyl aliphatic monomers such as esters of acrylic and methacrylic acids, acrylonitrile, and vinyl aromatic monomers such as styrene and substituted styrenes. Preferred polymers are styrenic polymers, optionally and preferably cross-linked, e.g. with divinyl benzene, and particles of such polymers are commercially available in a range of sizes and pore volumes from Dyno Specialty Polymers AS of Lillestrm, Norway. If desired, the particles may be functionalized, e.g. to provide surface acidic or basic groups (e.g. carboxyl or amino functions), for example to scavenge metal atoms from water reaching the particles so as to reduce scale formation, to promote particle adhesion to formation surfaces, to promote or hinder particle aggregation, etc. Again functionalized particles are available from Dyno Specialty Polymers AS. Preferably the polymer matrix of the impregnated particles has a softening point above the temperatures encountered down hole, e.g. one above 70° C., more preferably above 100° C., still more preferably above 150° C.

Generally where the particles are impregnated with hyperthermophilic organisms, they will also be impregnated with nutrients for the bacteria, e.g. sucrose, so that bacterial growth is promoted once the particles encounter water. Alternatively, so called "ultra microbacteria" may be used which are "starved" during the injection stage making them easier to penetrate deep into the formation. Subsequent administration of nutrients will then stimulate growth.

Examples of typical well treatment chemicals, precursors and generators are mentioned in the patent publications mentioned herein, the contents of all of which are hereby incorporated by reference.

Thus for example typical scale inhibitors include inorganic and organic phosphonates (e.g. sodium aminotrismethylene-phosphonate), polyaminocarboxylic acids or copolymers thereof, polyacrylamines, polycarboxylic acids, polysulphonic acids, phosphate esters, inorganic phosphates, polyacrylic acids, inulins (e.g. sodium carboxymethyl inulin), phytic acid and derivatives (especially carboxylic derivatives) thereof, polyaspartates, etc. The use of environmentally friendly scale inhibitors, e.g. inulins, phytic acid and derivatives thereof and polyaspartates, is especially preferred. Where the scale inhibitor is a polymer it may of course contain residues of one or more different comonomers, e.g. a copolymer of aspartic acid and proline.

Other beneficial microbial products include enzymes which are themselves able to synthesize well treatment chemicals such as scale inhibitors. It may be necessary to transform the bacteria with a plurality of genes coding for different enzymes which are involved in a synthetic pathway for a described well treatment chemical. Thus the well treatment chemical may be directly produced by the Archaea, i.e. an expression product, or indirectly produced as a result of metabolism or catabolism within the Archaea. Thus the well treatment chemical may be proteinaceous e.g. a polypeptide or glycoprotein but it need not be and could be a polysaccharide or a lipid.

Thus in a further aspect, the present invention also provides a method for the treatment of a hydrocarbon well which method comprises administering down an injection well thermophilic Archaea or other thermophilic bacteria or microorganisms capable of generating a desired compound such as acetic acid or an energy substrate such as methane, hydrogen or ethanol. Preferred features of this aspect, including the use of Archaea, hyperthermophilic organisms, or thermophilic organisms, either wild type or which have been genetically modified to produce desired products. The microorganisms introduced into the injection well may advantageously produce organic acids and/or chemicals involved in hydrate inhibition.

Where the hyperthermophilic organisms are placed within the formation, they are preferably applied as a dispersion in a liquid carrier. For pre- and post-completion application, the liquid carrier preferably comprises a non-aqueous organic liquid, e.g. a hydrocarbon or hydrocarbon mixture, typically a C3 to C15 hydrocarbon, or oil, e.g. crude oil. For curative treatment, i.e. after production has continued for some time, the liquid carrier may be aqueous or non-aqueous. Impregnation of the bacteria and if desired nutrients and/or other well treatment chemicals into porous carrier particles may be effected by any conventional manner, e.g. by contacting the particles with an aqueous or non-aqueous dispersion of the bacteria or other chemicals followed if necessary by solvent removal, e.g. by draining, drying or under vacuum.

However it is especially preferred to impregnate particles with the bacteria by slurry mixing, i.e. by adding a quantity of dispersion which is close to the pore volume of the particles, e.g. 0.8 to 1.2 times pore volume more preferably 0.9 to 1.1 times pore volume. Still more preferred is to impregnate the particles by a soaking procedure using a vacuum. The process may conveniently be performed in a rotavapor at 0-15 mbar at room temperature and continued at 50° C. until most of the water-phase has been removed. It is desirable to introduce bacteria into the pore system not only onto the surface. If desired particle loading may be increased by carrying out more than one impregnation step.

Various methods can be envisaged to sustain the microorganism population in situ. The microorganism can be immobilized in the porous matrix with nutrition packages or co-injected with nutrients into small porous particles which can then be injected deep (e.g. 2-l0m) into the formation. High concentration inoculates of the thermophilic bacteria can be introduced into the porous particles. Advantageously, some of the bacterial species which may be introduced are capable of producing viable spores in the well environment.

The invention also includes a bioreactor for cultivating hyperthermophilic organisms. The well treatment substrates and/or hyperthermophilic organisms are thus cultivated or made in the bioreactor and then applied to the hydrocarbon well. In a preferred embodiment, particles of the type described herein, i.e. porous impregnatable particles may be loaded with the products of the bioreactor. The bioreactor, which may be situated at or near the site of the borehole or remote from the borehole, may function to enable the production of any well treatment chemical, such as those described above. The organisms used in the bioreactor may be naturally occurring, e.g. naturally occurring bacteria or Archaea, as exemplified above that product well treatment chemical products are synthesized either though modifying or adding regulatory or structural sequences. Bioreactor as used herein refers to any system for the growth of cells in culture, namely microorganisms such as bacteria or Archaea. Nutrients can be supplied to the bioreactor and samples easily removed.

The product isolated from the organisms may be secreted or may be retained in the cell. In the case that the produce is secreted, it may be continuously removed from the cell culture medium, by removing the culture medium and replacing it with the fresh growth medium. The product may then be isolated from the growth medium using standard techniques. Alternatively, the microorganisms may be removed from the bioreactor and the product isolated following cell disruption, using techniques known in the art.

Accordingly, in some embodiments, the present invention provides methods of generating oil or energy substrates comprising delivering a composition comprising hyperthermophilic organisms to an oil bearing formation or other subterranean cavity such as a cave, mine or tunnel via an injection well. In some embodiments, the composition comprising hyperthermophilic organisms further comprises a component selected from the group consisting of energy substrate(s), mineral, salts, vitamins, amino acids, and/or microorganism extracts and combinations thereof. In some embodiments, the methods further comprise delivering a biomass to the oil bearing formation via an oil well. The biomass is preferably selected from the group consisting of sewage, agricultural waste products, brewery grain by-products, food waste, organic industry waste, whey, forestry waste, crops, grass, seaweed, plankton, algae, fish, fish waste, newsprint and combinations thereof. In some preferred embodiments, the biomass is liquefied prior to injection via the oil well. The present invention is not limited to any particular mechanism of action. Indeed, an understanding of the mechanism of action is not necessary to practice the present invention. Nonetheless, it is contemplated that in some embodiments, the hyperthermophilic organisms introduced into an oil bearing formation proliferate and produce acetic acid. The acetic acids makes the rocks of the oil bearing formation more porous thus allowing the recovery of additional oil in the formation. It is contemplated that delivery of additional energy substrates such as biomass will accelerate this process. It is further contemplated that in some embodiments, the oil bearing formation is geothermally heated to a temperature conducive to the growth of hyperthermophilic organisms. Thus, the oil bearing formation can be utilized as a reactor of the production of energy substrates from the degradation of biomass by hyperthermophilic organisms as described above in detail. In these embodiments, hydrogen, ethanol, and/or methane are recovered via wells or pipes inserted into the oil bearing formation into which hyperthermophilic organisms and biomass have been introduced.

It will be recognized that while the embodiments described above utilize hyperthermophilic organisms, the methods and systems of the present invention may also utilize thermophilic organisms. Suitable thermophilic organisms include, but are not limited to, *Thermoanaerobacterium saccharolyticum*, and members of *Geobacillus, Anaerocellum, Caldicellulosiruptor, Clostridium, Dictyoglomus, Fervidobacterium, Spirocheta* species.

E. Utilization of Acetate

As described in the examples, one of the main products of fermentation with the hyperthermophilic organisms is acetate. The present invention provides novel processes for utilizing acetate to produce energy.

In some embodiments, acetate produced by fermentation with hyperthermophilic organisms is used for the production of methane or biogas. In these embodiments, the acetate, preferably contained in liquid fermentation broth, is introduced into a bioreactor containing methanogenic microorganisms. Examples of methanogens that are useful in bioreactors of the present invention include, but are not limited to, *Methanosaeta* sp. and *Methanosarcina* sp. The methane produced by this process can subsequently be used to produce electricity or heat by known methods.

The use of a wide variety of bioreactors, also known as biodigesters, is contemplated. Examples include, but are not limited to, floating drum digesters, fixed dome digesters, Deenbandhu digesters, bag digesters, plug flow digesters, anaerobic filters, upflow anaerobic sludge blankets, and pit storage digestors. Full-scale plants that are suitable for use in the present invention can be purchased from providers such as Schmack AG, Schwandorf, DE. These systems may be modified to accept introduction acetate from the hyperthermophilic bioreactors of the present invention. In some preferred embodiments, the methanogen bioreactor is in fluid communication with the hyperthermophilic bioreactor. In some embodiments, the liquid fermentation broth from the hyperthermophilic bioreactor contains acetate and is delivered to the methanogen bioreactor. Preferably, the bioreactors are in fluid communication, but in alternative embodiments, the acetate-containing substrate may be delivered via tanker or other means. Exemplary systems are depicted in FIGS. 1 and 2.

Figure 2:
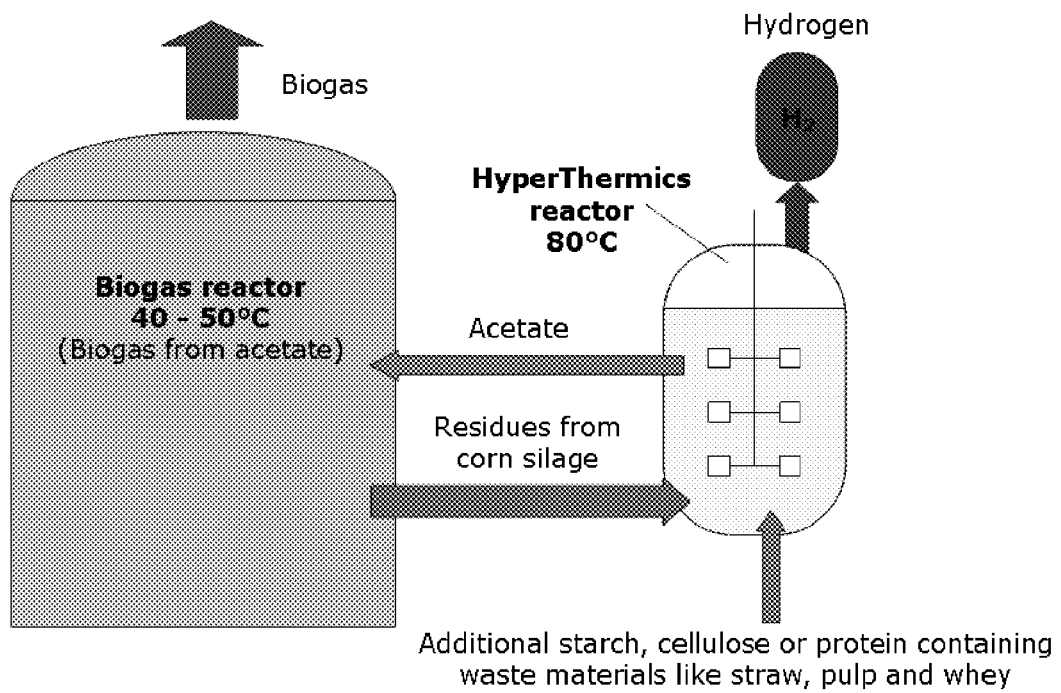
FIG. 2 depicts a bioreactor of the present invention coupled to a biogas production system.

According to FIGS. 1 and 2, biomass is input into a bioreactor containing hyperthermophilic microorganisms. The biomass is preferably provided in a liquid medium. In some embodiments, the biomass has been previously degraded by microorganisms (e.g., the biomass may be the residue from a biogas reactor as depicted), biomass that has not been previously degraded or fermented by a biological process, or a mixture of the two. As shown in FIGS. 1 and 2, degradation products from the hyperthermophilic bioreactor include $H_2$ and acetate. In some embodiments, acetate from the hyperthermophilic reactor is introduced into the biogas reactor. In some embodiments, the acetate is at least partially separated from the biomass residue in the hyperthermophilic reactor. In some embodiments, an aqueous solution comprising the acetate is introduced into the biogas reactor. In other embodiments, a slurry comprising the biomass residue and acetate is introduced into the biogas reactor. In some embodiments, the aqueous solution or slurry are pumped from the hyperthermophilic reactor into the biogas reactor. As described above, in some preferred embodiments, the aqueous solution or slurry have a NaCl concentration of less than about 0.2%. In some embodiments, $H_2$ is removed from the system, while in other embodiments, $H_2$ and other products including $CO_2$, are introduced into the biogas reactor. In some embodiments, the systems include a heat transfer system, such as the Organic Rankine Cycle depicted in FIG. 1. It is contemplated that production of acetate by degradation of biomass with hyperthermophilic microorganisms either before or after biogas production an increase the efficiency of use of a biomass material as compared to known biogas processes. Additional systems are described in FIG. 4, which depicts a system where two different hyperthermophilic organisms are used in conjunction with biogas production.

Figure 3:
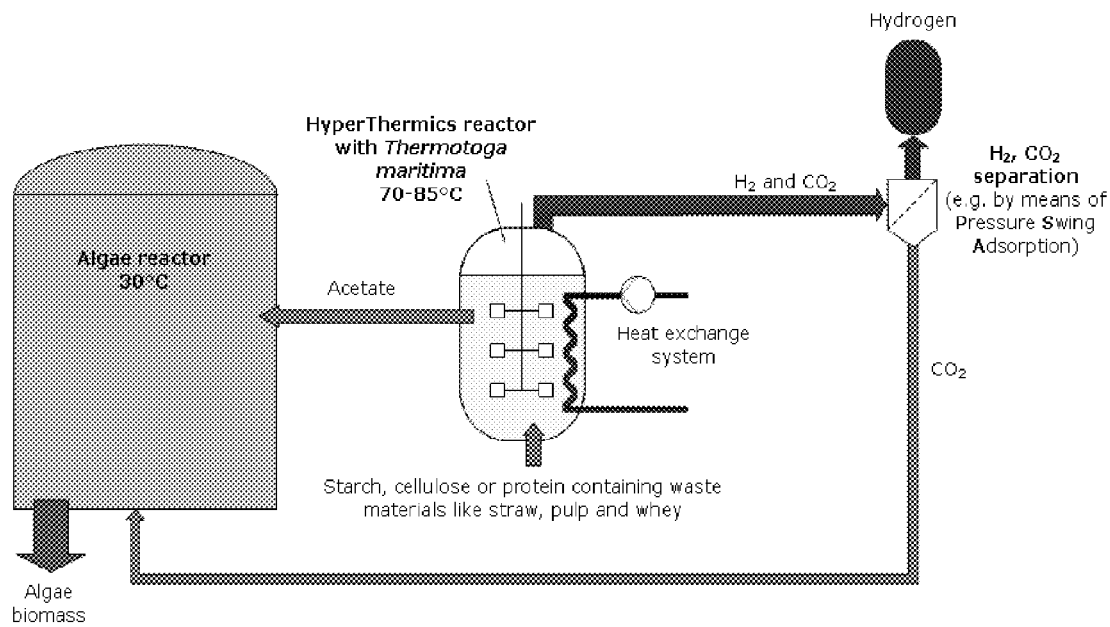
FIG. 3 shows a high temperature bioreactor and the use of the fermentation products of *Thermotoga* acetate and $CO_2$ as substrate for cultivation of algae. $H_2$ can be separated from $CO_2$ by pressure swing adsorption (psa)

In some embodiments, acetate, $CO_2$ and/or other degradation products produced by fermentation with hyperthermophilic organisms are used for the culture of algae (FIG. 3). In these embodiments, the degradation products (e.g., acetate), preferably contained in liquid fermentation broth, is introduced into a culture system for the production of algae. In some embodiments, the liquid fermentation broth from the hyperthermophilic bioreactor contains acetate and is delivered to the algae culture system. Preferably, the bioreactor and culture system are in fluid communication, but in alternative embodiments, the acetate-containing substrate may be delivered via tanker or other means. In preferred embodiments, algae grown is processed for the production of fatty acids which are then converted into biodiesel. A variety of methods are known in the art for accomplishing this conversion and for producing biodiesel and other energy substrates from algae.

Any suitable species of algae or prokaryotic cyanobacteria may be used in the present invention. In preferred embodiments, the algae is a microalgae, for example, a diatom (Bacillariophyceae), green algae (Chlorophyceae), or golden algae (Chrysophyceae). The algae may preferably grow in fresh or saline water. In some preferred embodiments, microalgae from one or more of the following genera are utilized: *Oscillatoria, Chlorococcum, Synechococcus, Amphora, Nannochloris, Chlorella, Nitzschia, Oocystis, Ankistrodesmus, Isochrysis, Dunaliella, Botryococcus*, and *Chaetocerus*.

In certain embodiments, algae of use to produce biodiesel may be genetically engineered (transgenic) to contain one or more isolated nucleic acid sequences that enhance oil production or provide other characteristics of use for algal culture, growth, harvesting or use. Methods of stably transforming algal species and compositions comprising isolated nucleic acids of use are well known in the art and any such methods and compositions may be used in the practice of the present invention. Exemplary transformation methods of use may include microprojectile bombardment, electroporation, protoplast fusion, PEG-mediated transformation, DNA-coated silicon carbide whiskers or use of viral mediated transformation (see, e.g., Sanford et al., 1993, Meth. Enzymol. 217:483-509; Dunahay et al., 1997, Meth. Molec. Biol. 62:503-9; U.S. Pat. Nos. 5,270,175; 5,661,017, incorporated herein by reference).

For example, U.S. Pat. No. 5,661,017 discloses methods for algal transformation of chlorophyll C-containing algae, such as the Bacillariophyceae, Chrysophyceae, Phaeophyceae, Xanthophyceae, Raphidophyceae, Prymnesiophyceae, Cryptophyceae, Cyclotella, Navicula, Cylindrotheca, Phaeodactylum, Amphora, Chaetoceros, Nitzschia or Thalassiosira. Compositions comprising nucleic acids of use, such as acetyl-CoA carboxylase, are also disclosed.

In various embodiments, algae may be separated from the medium and various algal components, such as oil, may be extracted using any method known in the art. For example, algae may be partially separated from the medium using a standing whirlpool circulation, harvesting vortex and/or sipper tubes. Alternatively, industrial scale commercial centrifuges or tricanters of large volume capacity may be used to supplement or in place of other separation methods. Such centrifuges may be obtained from known commercial sources (e.g., Cimbria Sket or IBG Monforts, Germany; Alfa Laval A/S, Denmark). Centrifugation, sedimentation and/or filtering may also be of use to purify oil from other algal components. Separation of algae from the aqueous medium may be facilitated by addition of flocculants, such as clay (e.g., particle size less than 2 microns), aluminum sulfate or polyacrylamide. In the presence of flocculants, algae may be separated by simple gravitational settling, or may be more easily separated by centrifugation. Flocculent-based separation of algae is disclosed, for example, in U.S. Patent Appl. Publ. No. 20020079270, incorporated herein by reference.

The skilled artisan will realize that any method known in the art for separating cells, such as algae, from liquid medium may be utilized. For example, U.S. Patent Appl. Publ. No. 20040121447 and U.S. Pat. No. 6,524,486, each incorporated herein by reference, disclose a tangential flow filter device and apparatus for partially separating algae from an aqueous medium. Other methods for algal separation from medium have been disclosed in U.S. Pat. Nos. 5,910,254 and 6,524,486, each incorporated herein by reference. Other published methods for algal separation and/or extraction may also be used. (See, e.g., Rose et al., Water Science and Technology 1992, 25:319-327; Smith et al., Northwest Science, 1968, 42:165-171; Moulton et al., Hydrobiologia 1990, 204/205: 401-408; Borowitzka et al., Bulletin of Marine Science, 1990, 47:244-252; Honeycutt, Biotechnology and Bioengineering Symp. 1983, 13:567-575).

In various embodiments, algae may be disrupted to facilitate separation of oil and other components. Any method known for cell disruption may be utilized, such as ultrasonication, French press, osmotic shock, mechanical shear force, cold press, thermal shock, rotor-stator disruptors, valve-type processors, fixed geometry processors, nitrogen decompression or any other known method. High capacity commercial cell disruptors may be purchased from known sources. (E.g., GEA Niro Inc., Columbia, Md.; Constant Systems Ltd., Daventry, England; Microfluidics, Newton, Mass.) Methods for rupturing microalgae in aqueous suspension are disclosed, for example, in U.S. Pat. No. 6,000,551, incorporated herein by reference.

A variety of methods for conversion of photosynthetic derived materials into biodiesel are known in the art and any such known method may be used in the practice of the instant invention. For example, the algae may be harvested, separated from the liquid medium, lysed and the oil content separated. The algal-produced oil will be rich in triglycerides. Such oils may be converted into biodiesel using well-known methods, such as the Connemann process (see, e.g., U.S. Pat. No. 5,354,878, incorporated herein by reference). Standard transesterification processes involve an alkaline catalyzed transesterification reaction between the triglyceride and an alcohol, typically methanol. The fatty acids of the triglyceride are transferred to methanol, producing alkyl esters (biodiesel) and releasing glycerol. The glycerol is removed and may be used for other purposes.

Preferred embodiments may involve the use of the Connemann process (U.S. Pat. No. 5,354,878). In contrast to batch reaction methods (e.g., J. Am. Oil Soc. 61:343, 1984), the Connemann process utilizes continuous flow of the reaction mixture through reactor columns, in which the flow rate is lower than the sinking rate of glycerine. This results in the continuous separation of glycerine from the biodiesel. The reaction mixture may be processed through further reactor columns to complete the transesterification process. Residual methanol, glycerine, free fatty acids and catalyst may be removed by aqueous extraction. The Connemann process is well-established for production of biodiesel from plant sources such as rapeseed oil and as of 2003 was used in Germany for production of about 1 million tons of biodiesel per year (Bockey, "Biodiesel production and marketing in Germany.")

The algae may be cultured in a variety of systems. In some embodiments, the algae are cultured in fresh water or saline open ponds. In other embodiments, the algae are cultured in closed bioreactor systems such as fiber optic filaments, polymer tubing, and polymer bags.

F. Carbon Credit Trading

In some embodiments, the present invention provides methods for generating carbon credits for trading in established carbon credit trading programs such as those established under the Kyoto protocol. The European Union Emission Trading System (EU ETS), which began operation in January 2005, is the largest multi-national, multi-sector greenhouse gas emissions trading scheme in the world. The system was set up as the EU's response to the Kyoto Protocol to the United Nations Framework Convention on Climate Change which was negotiated in 1997 and ratified in 2005. It is a commitment among participating industrialised nations to curb the rise in global temperature by abating their emissions of six greenhouse gases including carbon dioxide, methane, nitrous oxide, sulfur hexafluoride, perfluorocarbons (PFCs) and hydrofluorocarbons (HFCs). To date, 162 nations have ratified the agreement. Notable exceptions are the United States and Australia. Furthermore, two of the fastest growing economies, India and China, are not required to reduce their carbon emissions under the current agreement.

The Kyoto Protocol provides three implementation mechanisms to regulate greenhouse gas emissions. The first, International Emissions Trading (IET), permits countries below their current emissions limits to sell their excess allowances to other countries on the open market. The second, Joint Implementation (JI), allows investors from industrialised countries financing greenhouse gas emissions reduction projects in other industrialised countries to receive emission credits called "emissions reduction units" (ERUs). The third, Clean Development Mechanism (CDM), lets investors from industrialised countries accumulate "certified emission reduction units" (CERs) for helping finance carbon reduction projects in developing countries.

The EU ETS exists in two phases and encompasses all of the high use energy and power sectors. The first phase, which started in 2005 and will end in 2007, allows for the trade of $CO_2$ allowances with the potential to expand into the other five greenhouse gasses. So far, it has set caps on the emissions of 12,000 to 15,000 industrial installations across Europe. It covers 45% of emission activities including power, concrete, pulp, paper, and ferrous metals. The second phase, from 2008 to 2012, could possibly cover all greenhouse gases and installations, and will include JI and CDM credits in the market. It is important to note that in the first phase an amendment called the Linking Directive was implemented which enabled installations to use CERs and ERUs from JI and CDM to meet their emission targets.

The EU ETS is monitored and regulated by the EU Commission (EUC). In both phases, the EUC places limitations on GHG (greenhouse gas) which are satisfied through the trading of EU emission allowances (EUAs). The goal is to force companies to find the lowest cost of abatement by decreasing their GHG internally and selling any unused EUAs into the market. During the first phase, the EUC imposes a penalty of €40 per ton of $CO_2$ for installations that emit more than their target limit. In addition, these installations must acquire their excess emissions in the market. This penalty will go to €100 per ton of $CO_2$ in the second phase.

Participating countries in the EU ETS submit their target GHG reductions through National Allocation Plans (NAPs) which then are approved by the EUC. According to the Norwegian consultant Point Carbon, during the first phase of the EU ETS, the EUC approved circa 6.3 billion allowances and allowed for another 2.1 billion to be distributed each year.

As one example of an established system, the European Bank for Reconstruction and Development (EBRD) and the European Investment Bank (EIB) established the Multilateral Carbon Credit Fund (MCCF) for countries from Central Europe to Central Asia.

By joining the MCCF, private and public companies as well as EBRD and EIB shareholder countries can purchase carbon credits from emission reduction projects financed by the EIB or EBRD to meet their mandatory or voluntary greenhouse gas emission reduction targets.

In addition to the project credits, countries can also participate via the MCCF in green investment schemes. This is an innovative way to facilitate government-to-government trade in carbon credits, whereby the selling country uses the revenue from the sale of carbon credits to support investments in climate-friendly projects. Carbon credits can be generated from a large variety of project types, all of which reduce or avoid GHG emissions. These include credits produced from renewable energy such as wind, hydro, biogas (from landfills/wastewater) and biomass.

In some embodiments, the present invention generates carbon credits for trading by utilizing biomass. In other embodiments, the present invention generates carbon credits for trading by utilizing materials that would otherwise create methane that is subsequently released into the atmosphere, such as manure, sewage, waste water, landfilled materials and the like. The present invention is not limited to any particular mechanism of action. Indeed, an understanding of the mechanism of action is not needed to practice the present invention. Nevertheless, it is contemplates that the use of hyperthermophilic organisms in an anaerobic degradation process is highly efficient for reducing carbon emissions, and in particular emissions of carbon dioxide. In particular, the use of anaerobic degradation reduces the amount carbon dioxide released from biomass by about five-fold as compared to aerobic degradation or fermentation processes.

In some embodiments, the present invention provides a system wherein energy is produced by degradation of biomass with hyperthermophilic organisms, and resulting carbon credits generated through the use of the system are used to offset greenhouse gas emissions by conventional energy production systems such as combustion of coal, natural gas, and oil. In some embodiments, the energy production systems are under the control of a single entity, while in other embodiments, the energy production systems are under the control of separate entities and the carbon credits are purchased by or traded to the entity generating power by conventional means with fossil fuels.

EXPERIMENTAL

1. Selection of Hyperthermophilic Organisms for Degradation Processes

In this example, strains of hyperthermophilic organisms from the genera *Pyrococcus, Thermococcus, Palaeococcus, Aeropyrum pernix, Sulfolobus, Pyrobaculum, Pyrolobus, Pyrodictium, Thermus, Bacillus stearothermophilus, Metallosphaera, Anaerocellum, Thermoactinomyces, Thermotoga, Fervidobacterium* and *Geotoga* are selected and screened for the ability to produce fermentation byproducts ethanol, methanol and hydrogen. Briefly, seed inoculums are prepared by culturing the cells in YT medium (yeast extract [2.0 g/liter], tryptone [4.0 g/liter], $Na_2S_2O_3$ [0.61 g/liter], and ASN-III salts) for 48 h. Flasks containing base medium (tryptone (4.0 g/liter), $Na_2S_2O_3$ (0.61 g/liter), and ASW-III salts (artificial seawater salts containing NaCl [29.8 g/liter], $MgCl_2$ [1.1 g/liter], $MgSO_4$ [2.0 g/liter], $CaCl_2$ [0.45 g/liter], KCl [0.6 g/liter], and $Na_2CO_3$ [0.024 g/liter]) (pH 7.0)) supplemented with specific carbohydrates (glucose, xylose, arabinose, galactose, and/or mannose) (3.0 g/liter) are inoculated with 10% seed inoculums. The flasks are then purged with prepurified $N_2$ and the incubation is carried out at 80° C.-103° C. in a rotary shaker at 150 rpm. Cell growth is observed by monitoring optical density at 570 nm ($OD_{570}$) or by direct microscopic counting in a cell chamber. Samples are collected from the headspace and culture medium and analyzed by GC for fermentation products.

2. Growth of *Pyrococcus furiosus* and *Thermotoga maritima* on Waste Materials and Biomass Substrates The hyperthermophilic archaeon *Pyrococcus furiosus* (growth range 67-103° C., optimal growth at 100° C.) uses simple and complex carbohydrates and converts them to acetate, to $CO_2$ and to $H_2$. Only in the presence of elemental sulphur (S°), $H_2$ is used to reduce sulphur to $H_2S$. An exponentially growing culture produces ~1 µmol $ml^{-1}h^{-1}$ $H_2$ (Schut et al., 2007, J. Bacteriol 189, 4431-4441). Growth experiments in the laboratory have shown that the strain requires peptone and yeast extract (as protein and vitamin source) in addition for good growth ($2.2 \times 10^8$ cells/ml). On starch as sole carbon source only poor growth was observed (~$5 \times 10^7$ cells/ml).

*Thermotoga maritima* is an obligately anaerobic hyperthermophilic bacterium growing between 55-90° C. (growth optimum at 80° C.). Like *Pyrococcus* it is of marine origin and is cultivated in media resembling seawater. *Thermotoga* is an obligate heterotroph preferentially fermenting carbohydrates or complex organic matter. Fermentation of glucose by cell suspensions of *Thermotoga* yielded 118 mol L-(+) lactate, 47 mol acetate, 54 mol $CO_2$ and 9 mol $H_2$ (Huber et al., 1986, Arch. Microbiol. 144, 324-333). Some of the members of the *Thermotogales* like *Fervidobacterium nodosum* (Patel et al., 1985 Arch. Microbiol. 141, 63-69) and *Fervidobacterium islandicum* (Huber et al., Arch. Microbiol. 1990, 154, 105-111) have been described to produce also ethanol. *F. nodosum* forms after 13 h growth on glucose ~25 µmol ethanol per 10 ml culture broth (Patel et al., 1985). A quantitative analysis of fermentation products (micromole of product formed per 10 ml culture) of *T. nodosum* grown on glucose revealed: Ethanol 10, acetate 115, lactate 162, $CO_2$ 120 and $H_2$ 160 per 133 micromol glucose consumed. For the first time, below we demonstrate ethanol production by *Thermotoga* sp., in particular *Thermotoga maritima*.

Both organisms do not completely oxidize organic matter to $CO_2$. The carbon of the substrate is in part converted to soluble compounds like acetate and lactate. Both organism produce low amounts of hydrogen and soluble compounds like acetate. Some members of the *Thermotogales* have been described to produce ethanol in addition (*Fervidobacterium*). Thus these anaerobic organisms have the potential to synthesize energy rich compounds like $H_2$ and ethanol. The amount of $CO_2$ produced during anaerobic degradation of biomass is significantly lower than $CO_2$ release during aerobic processes which lead to complete oxidation of organic matter to $CO_2$. Methane formation will not occur during this process when pure cultures are used or when the waste substrate is sterilized. Otherwise methane might be formed from the end products formed by degradation of organic matter from *Thermotoga* and *Pyrococcus* ($H_2/CO_2$ and acetate). Acetate can be also converted to methane but no hyperthermophilic methanogen growing on acetate has been described. Therefore, it is unlikely that methane is formed from acetate when the fermentation will be conducted at temperatures between 80 and 100° C.

The objective was to investigate the potential of *P. furiosus* and *T. maritima* as model systems for the degradation of waste products and to investigate their ability to produce and to release heat during growth. The degradation of various waste products was studied in 100 l batch cultures. The energy release during growth was measured in a 10 l glass fermentor. The heating system of this fermentor was modified to lower the input of energy. The fermentor was isolated by the use of an aluminium containing shell and further isolated by styrene. As a control, heat release by a 10 l culture of *Saccharomyces cerevisiae* was also measured using this system.

Ethanol Production by *Thermotoga maritima*

Detailed formulations of the culture media are provided below.

Since ethanol production has been described for some members of *Thermotogales* like *Fervidobacterium* we analyzed ethanol production by *T. maritima* and by a variety of other species of the *Thermotogales* during growth on starch and cellulose as substrate. For *Thermotoga maritima* we found the production of 86 mg ethanol per liter in an optimized culture grown on starch (cell density in the stationary growth phase was $3.5 \times 10^9$ cells×$ml^{-1}$). The other *Thermotoga*-strains produced ethanol as well. The amount of formed ethanol corresponded roughly to the cell density in the cultures. Ethanol in the vapour of the cultures was not determined, therefore the actual ethanol production by *Thermotoga* might be higher.

Heat Production During Growth

It is known that large fermentors used for biotechnological processes like ethanol fermentation by yeast require cooling due to the energy released by growing yeast. To control the system for the detection of heat production we grew yeast anaerobically at 30° C. During 95 h after inoculation of the medium no external energy input was required to keep the growth temperature at 30° C. and the temperature of the culture medium was even increased by 0.5° C. This finding suggests that the detecting system is suitable to measure energy release by microorganisms. To confirm the validity of our measurement it is advisable to repeat the experiment in an air conditioned room (room temperature fixed at 20° C.).

In a further optimized system heat production during growth of yeast in a 10 l fermentor was measured accurately. A yeast culture with a cell density of $1 \times 10^8$ cells/ml produced 3.2 W in a 10 l fermentor. First experiments with *Thermotoga* and *Pyrococcus* in the 10 l scale did not allow the measurement of heat release because growth of these bacteria in the 10 l fermentor was too poor in the initial experiments (only $2 \times 10^8$ cells $ml^{-1}$). Yeast cells have about 100 times the volume of bacterial cells and therefore $\sim 10^{10}$ bacterial cells are required to yield the same biomass as $10^8$ cells of yeast. But bacteria are known to have a $\sim 10$ fold higher metabolic rate than yeast. Therefore, $10^9$ bacteria will produce $\sim$ the same amount of heat than $10^8$ cells of yeast.

An optimized *Thermotoga* or *Pyrococcus* culture containing $10^{10}$ cells per ml will produce $\sim 32$ kW of heat in a 10 m$^3$ fermentor. A 1000 m$^3$ facility based on degradation of waste products by hyperthermophilic cultures will produce $\sim 3.2$ MW of heat.

3. Growth Medium for *Pyrococcus furiosus*: ½ SME

½ SME

| Component | Amount |
| --- | --- |
| SME | 500.0 ml |
| KH$_2$PO$_4$ | 0.5 g |
| (NH$_4$)$_2$SO$_4$ | 0.25 g |
| Wolfe's mineral elixir/10x/pH 1.0 | 1.0 ml |
| Resazurin, 0.1% solution | 1.0 ml |
| Na$_2$S × 7-9H$_2$O | 0.5 g |
| H$_2$O 2x distilled, add to a final volume of | 1000.0 ml |

Synthetic Seawater—SME

| Component | Amount | Concentration |
| --- | --- | --- |
| NaCl | 27.7 g | 473.99 mM |
| MgSO$_4$ × 7H$_2$O | 7.0 g | 28.4 mM |
| MgCl$_2$ × 6H$_2$O | 5.5 g | 27.1 mM |
| CaCl$_2$ × 2H$_2$O | 0.75 g | 5.1 mM |
| KCl | 0.65 g | 8.7 mM |
| NaBr | 0.1 g | 0.97 mM |
| H$_3$BO$_3$ | 0.03 g | 0.49 mM |
| SrCl$_2$ × 6H$_2$O | 0.015 g | 0.056 mM |
| KJ-Lsg., 0.05% ig | 0.1 ml | 0.30 µM |
| H$_2$O 2x distilled, add to a final volume of | 1000.0 ml | |

Wolfe's Mineral Elixir 10x/pH 1.0

| Component | Amount | Concentration |
| --- | --- | --- |
| MgSO$_4$ × 7H$_2$O | 30.0 g | 121.70 mM |
| MnSO$_4$ × H$_2$O | 5.0 g | 29.60 mM |
| NaCl | 10.0 g | 171.10 mM |
| FeSO$_4$ × 7H$_2$O | 1.0 g | 3.60 mM |
| CoSO$_4$ × 7H$_2$O | 1.8 g | 6.40 mM |
| CaCl$_2$ × 2H$_2$O | 1.0 g | 6.80 mM |
| ZnSO$_4$ × 7H$_2$O | 1.8 g | 6.30 mM |
| CuSO$_4$ × 5H$_2$O | 0.1 g | 0.40 mM |
| KAl (SO$_4$)$_2$ × 12H$_2$O | 0.18 g | 0.38 mM |
| H$_3$BO$_3$ | 0.1 g | 1.62 mM |
| Na$_2$MoO$_4$ × 2H$_2$O | 0.1 g | 0.41 mM |
| (NH$_4$)$_2$Ni(SO$_4$)$_2$ × 6H$_2$O | 2.80 g | 7.09 mM |
| Na$_2$WO$_4$ × 2H$_2$O | 0.1 g | 0.30 mM |
| Na$_2$SeO$_4$ | 0.1 g | 0.53 mM |
| H$_2$O 2x distilled, add to a final volume of | 1000.0 ml | |

In rich medium, the following organic substrates were added:

| Component | Amount |
| --- | --- |
| Yeast extract (Difco) | 0.05% (w/v) |
| Starch (Merck) | 0.5% (w/v) |

Adjusted pH value of medium: pH 6.5
Headspace: N$_2$

To study utilization of waste products the organic components of the medium were replaced by various waste materials (see below).

4. *Thermotoga* mM-1-Medium

MM-I-Medium

| Component | Amount |
| --- | --- |
| SME | 250.0 ml |
| KH$_2$PO$_4$ | 0.5 g |
| (NH$_4$)$_2$SO$_4$ | 0.5 g |
| NaHCO$_3$ | 0.1 g |
| Wolfe's mineral elixir, 10x/pH 1.0 | 1.5 ml |
| Resazurin, 0.1% solution | 1.0 ml |
| Na$_2$S × 7-9H$_2$O | 0.5 g |
| H$_2$O 2x distilled, add to a final volume of | 1000.0 ml |

Synthetic Seawater—SME

| Component | Amount | Concentration |
| --- | --- | --- |
| NaCl | 27.7 g | 473.99 mM |
| MgSO$_4$ × 7H$_2$O | 7.0 g | 28.4 mM |
| MgCl$_2$ × 6H$_2$O | 5.5 g | 27.1 mM |
| CaCl$_2$ × 2H$_2$O | 0.75 g | 5.1 mM |
| KCl | 0.65 g | 8.7 mM |
| NaBr | 0.1 g | 0.97 mM |
| H$_3$BO$_3$ | 0.03 g | 0.49 mM |
| SrCl$_2$ × 6H$_2$O | 0.015 g | 0.056 mM |
| KJ-solution., 0.05% (w/v) | 0.1 ml | 0.30 µM |
| H$_2$O 2x distilled, add to a final volume of | 1000.0 ml | |

Wolfe's Mineral Elixir 10x/pH 1.0

| Compound | Amount | Concentration |
| --- | --- | --- |
| MgSO$_4$ × 7H$_2$O | 30.0 g | 121.70 mM |
| MnSO$_4$ × H$_2$O | 5.0 g | 29.60 mM |
| NaCl | 10.0 g | 171.10 mM |
| FeSO$_4$ × 7H$_2$O | 1.0 g | 3.0 mM |
| CoSO$_4$ × 7H$_2$O | 1.8 g | 6.40 mM |
| CaCl$_2$ × 2H$_2$O | 1.0 g | 6.80 mM |
| ZnSO$_4$ × 7H$_2$O | 1.8 g | 6.30 mM |

-continued

| Compound | Amount | Concentration |
|---|---|---|
| $CuSO_4 \times 5H_2O$ | 0.1 g | 0.40 mM |
| $KAl(SO_4)_2 \times 12H_2O$ | 0.18 g | 0.38 mM |
| $H_3BO_3$ | 0.1 g | 1.62 mM |
| $Na_2MoO_4 \times 2H_2O$ | 0.1 g | 0.41 mM |
| $(NH_4)_2Ni(SO_4)_2 \times 6H_2O$ | 2.80 g | 7.09 mM |
| $Na_2WO_4 \times 2H_2O$ | 0.1 g | 0.30 mM |
| $Na_2SeO_4$ | 0.1 g | 0.53 mM |
| $H_2O$ 2x distilled, add to a final volume of | 1000.0 ml | |

In rich medium, the following organic substrates were added:

| Component | Amount |
|---|---|
| Yeast extract (Difco) | 0.05% (w/v) |
| Starch (Merck) | 0.5% (w/v) |

Adjusted pH value of medium: pH 7.0
Headspace: $N_2$

To study utilization of waste products the organic components of the medium were replaced by various waste materials (see below).

5. Production of Hydrogen, Acetate and Ethanol by *Thermotoga maritima* in Large Scale Cultures

*T. maritima* was grown in MM-I medium containing 0.5% starch and 0.05% yeast extract (YE) as substrates. During the fermentation additional starch (1.0%) was pumped in the bioreactor to avoid substrate deficiency. Hydrogen formed by the microorganisms was removed from the bioreactor by flushing with nitrogen to avoid $H_2$ growth inhibition. This $H_2$ stripping was started at a cell density of $5 \times 10^7$-$1 \times 10^8$ cells/ml. To determine the hydrogen production rate of *Thermotoga* the exhaust gas was analyzed by gas chromatography. The pH value of the culture was kept constant at 7.00 by an automatic pH titration system. This system measures the pH value permanently. When the pH decreases to 6.99 (due to acid formation by the microorganisms) the system pumps NaOH into the bioreactor until the setpoint value of 7.00 is reached again. The maximum cell density and the amount of fermentation products on starch as substrate were determined. This is a basis for analysis of starch containing waste materials as substrates. The results can also be used as references for the degradation of other organic waste products.

*T. maritima* grew to a final cell density of $3.5 \times 10^9$ cells/ml. Over a period of 43 hours the microorganisms produced 25.5 mM acetate and 1.9 mM ethanol. The $H_2$ production was monitored from one hour after stripping started until the end of fermentation. This was a period of 26 hours at which *Thermotoga* produced 50.6 mM $H_2$ (50.6 mmol $H_2$ per liter of liquid culture). This is 1133 ml $H_2$ per liter of liquid culture. So the average $H_2$ production rate was 44 ml per hour and per liter of liquid culture (ml/h/L). The maximum $H_2$ production rate measured was 51 ml/h/L.

6. *Thermotoga maritima* Grows on Starch Containing Waste Products

*T. maritima* was grown on 3.0% (w/v) pulp (from potato production) as substrate. Thereby the microorganisms grew to a final cell density of $1.1 \times 10^8$ cells/ml. This experiment was performed without automatic pH control and without additional substrate feed (no pH control, no feed).

7. *Thermotoga maritima* Grows on Mixtures of Starch Containing and Other Organic Waste Materials

*T. maritima* was grown on a mixture of 3.0% (w/v) pulp and 3.0% (v/v) whey (no pH control, no feed). On these substrates *Thermotoga* grew to a final cell density of $1.0 \times 10^8$ cells/ml. A mixture of 3.0% (w/v) pulp and 1.0% (w/v) fish innards was also tested. But no growth was observed on this substrate mixture.

8. *Thermotoga maritima* Grows on Cellulose as Substrate

*T. maritima* was grown in MM-I medium containing 0.5% cellulose (Roth) and 0.05% yeast extract (YE) as substrates. During the fermentation additional cellulose (0.5%) was pumped in the bioreactor to avoid substrate deficiency. $H_2$ stripping and pH titration was performed as described above (see 5.). The maximum cell density and the amount of fermentation products were determined to get references for degradation of cellulose containing substrates/waste products.

*T. maritima* grew to a final cell density of $1.0 \times 10^8$ cells/ml. Over a period of 88 hours the microorganisms produced 1.3 mM acetate and 0.02 mM ethanol. The $H_2$ production was monitored for 48 hours after stripping started. In this period of time *Thermotoga* produced 1.9 mM hydrogen (1.9 mmol $H_2$ per liter of liquid culture). This is 43 ml $H_2$ per liter of liquid culture. So the average $H_2$ production rate was 0.90 ml$\times$$h^{-1}l^{-1}$. The maximum $H_2$ production rate measured was 1.62 ml$\times$$h^{-1}l^1$.

9. *Thermotoga maritima* Grows on Cellulose Containing Substrates/Waste Materials When *T. maritima* was grown on 5% (w/v) grain residues as substrate the culture reached a final cell density of $8.0 \times 10^6$ cells/ml (no pH control, no feed).

On 1.5% (w/v) sawdust a final cell density of $1.7 \times 10^7$ cells/ml was observed (no pH control, no feed). When the sawdust was milled in order to enlarge it's surface and to improve the accessibility of cellulose, the final cell density increased to $5.6 \times 10^7$ cells/ml.

Another tested substrate was fermented corn/grass silage. This was from an anaerobic biogas plant that produces methane out of a mixture of ⅔ corn silage and ⅓ grass silage. After the fermentation the utilized substrates are separated in a solid and a liquid phase. 4% (w/v) of the liquid phase was used as substrate for *T. maritima* (no pH control, no feed). Thereby the culture reached a final cell density of $6.0 \times 10^6$ cells/ml.

When 5% (w/v) of this fermented corn/grass silage (liquid phase) in combination with 0.5% (w/v) fresh (not fermented) corn silage was used as substrate, the final cell density was $6.3 \times 10^8$ cells/ml (no pH control, no feed). So the addition of a small amount of fresh silage resulted in a 100 fold increase in cell density. The cell density on a mixture of fermented and not fermented silage as substrate was 6 times higher than on pure cellulose.

Another suitable substrate for growth of *T. maritima* was 5% (w/v) of a fermented mixture of corn silage and poultry manure. This is the liquid phase outflow of a biogas plant in which a consortium of bacteria and methanogens metabolize a mixture of corn silage and poultry manure. On this substrate *Thermotoga* reached a final cell density of $1.0 \times 10^7$ cells/ml (no pH control, no feed).

10. *Thermotoga maritima* Grows on a Mixture of Cellulose Containing Substrates and Other Waste Materials

*Thermotoga maritima* was grown on a mixture of 5% (w/v) grain residues and 10% (v/v) whey (no pH control, no feed). On this substrate mixture the microorganisms grew to a final cell density of $1.4 \times 10^8$ cells/ml. So the addition of whey to the grain residue substrate resulted in an almost 20 fold increase of cell density (compare 9.).

When 5% (w/v) grain residues were combined with 0.9% (w/v) fish innards as substrates, even better growth was observed. Thereby *Thermotoga* reached a final cell density of $2.0 \times 10^8$ cells/ml (no pH control, no feed).

Another tested substrate mixture was 1.5% (w/v) sawdust and 4% (w/v) whey. This resulted in a final cell density of $2.8 \times 10^7$ cells/ml (no pH control, no feed). Here the cell density is lower than on the above mentioned mixtures, but it is higher compared to growth on pure sawdust (see 9.).

The substrate mixture that led to highest growth of *T. maritima* was 5% (w/v) fermented corn/grass silage, 0.5% (w/v) fresh (not fermented) corn silage and 8% (w/v) whey (no pH control). In this experiment the microorganisms were grown on the silage substrates until they reached the stationary phase of growth ($6.3 \times 10^8$ cells/ml). Then whey was added, which resulted in further growth to a final cell density of $1.1 \times 10^9$ cells/ml. This is 10 times more than on pure cellulose as substrate (see 8.) and ⅓ of the maximum cell density on starch (see 5.). Analysis of the fermentation products revealed the following results:

Over a period of 47 hours 17.0 mM of acetate and 4.3 mM of ethanol were produced. This is much more as on pure cellulose. Compared to growth on pure starch the amount of acetate was ⅓ lower but the amount of ethanol was more than 2 times higher. The hydrogen production was monitored for 27 hours. During this period of time *T. maritima* produced 24.8 mM $H_2$ (24.8 mmol $H_2$ per liter of liquid culture). This is 556 ml per liter of liquid culture. So the average $H_2$ production rate was 21 ml per hour and per liter of liquid culture (ml/h/L). The maximum $H_2$ production rate measured was 26.4 ml/h/L. These values are much higher as with pure cellulose as substrate (see 8.). Compared to growth on pure starch the hydrogen production is one half lower.

*Thermotoga maritima* also grew on 5% (w/v) of a fermented mixture of corn silage and poultry manure mixed with 4% (w/v) whey (no pH control, no feed). The final cell density on this substrate mixture was $2.6 \times 10^7$ cells/ml. When whey was added after the cells reached the stationary phase of growth on the fermented silage/poultry manure substrate, the final cell density was even much higher: $2.0 \times 10^8$ cells/ml. When whey was in the initial medium and more whey (12%) was added when the stationary phase of growth was reached, the maximum cell density was advanced to $4.0 \times 10^8$ cells/ml.

11. *Thermotoga maritima* Grows on Lactose Containing Substrates

*Thermotoga maritima* grew on 4% (w/v) whey to a final cell density of $7.0 \times 10^6$ cells/ml (no pH control, no feed). Whey consists mainly of lactose, proteins and some vitamins. Pure whey seems not to be a good substrate for *T. maritima* but in combination with other substrates it facilitates growth to high cell densities (see 10.).

12. *Thermotoga maritima* Grows on Newsprint as Substrate

This experiment was not performed in a bioreactor but in 590 ml glass bottles. So no pH control, no additional substrate feed and no $H_2$ stripping could be performed. To investigate whether *T. maritima* is able to grow on newsprint the following samples were prepared:

| | |
|---|---|
| Sample 1 (control): | 150 ml MM-I medium + 0.05% yeast extract (YE) |
| Sample 2: | 150 ml MM-I medium + 0.05% yeast extract + 5% (w/v) newsprint without ink |
| Sample 3: | 150 ml MM-I medium + 0.05% yeast extract + 5% (w/v) newsprint with ink |

Results:

*Thermotoga maritima* shows very poor growth on MM-I medium with 0.05% YE (source of vitamins), as there are almost no substrates available. In contrast the cells grow very well in the same medium containing 5% (w/v) newsprint. So *T. maritima* can utilize newsprint as substrate. Growth is even better when newsprint with ink is applied.

| Sample No. | Newsprint | Inoculated cell density | Cell density after 2 days incubation | Cell density after 3 days incubation |
|---|---|---|---|---|
| 1 (control) | no | $3.9 \times 10^5$/ml | $4.1 \times 10^6$/ml | $4.1 \times 10^6$/ml |
| 2 | without ink | $3.9 \times 10^5$/ml | $1.5 \times 10^8$/ml | $1.5 \times 10^8$/ml |
| 3 | with ink | $3.9 \times 10^5$/ml | $2.5 \times 10^8$/ml | $2.6 \times 10^8$/ml |

13. *Thermotoga maritima* Grows on Straw as Substrate

*T. maritima* was grown on a new substrate, namely straw with later addition of whey in a 100 l bioreactor with pH control. The substrate was milled to make it better accessible to microbial attack and to avoid wrapping of the long straw fibers around the stirrer, pH electrode, etc. $N_2$-stripping was started and whey added before the end of the exponential growth phase.

An unexpectedly high cell density and short generation time was reached (cell density=$7.4 \times 10^8$ cells/ml, generation time=1.2 h). The hydrogen production rate dropped rapidly after the beginning of the whey addition and started to raise again 4 hours after the addition of whey. Approx. 24 hours after reaching the stationary growth phase, the cell density began to rise exponentially and stopped at a cell density of $1.9 \times 10^9$ cells/ml. This incident is possibly a sign of the appearance of a *Thermotoga* mutant which is capable of digesting cellulose in a more efficient manner.

14. Production of Hydrogen and Acetate by *Pyrococcus furiosus* in Large Scale Cultures

*Pyrococcus furiosus* was grown in ½ SME medium containing 0.5% (w/v) starch and 0.05% (w/v) yeast extract as substrates. During growth of *Pyrococcus* additional starch (0.5%) was pumped in the bioreactor to avoid substrate deficiency. Hydrogen produced by the microorganisms was stripped by flushing with nitrogen to avoid $H_2$ growth inhibition. The stripping was started when the culture reached a cell density of $5 \times 10^7$-$1 \times 10^8$ cells/ml. Exhaust gas analysis and automatic pH control were performed as already described for *T. maritima* (see 5.). The maximum cell density and the amounts of produced end products can be used as references for the degradation of organic waste materials.

*P. furiosus* grew to a final cell density of $1.1 \times 10^9$ cells/ml. Over a period of 48.5 hours the microorganisms produced 39.5 mM acetate and 0.17 mM ethanol. The $H_2$ production was monitored for 37 hours after flushing with nitrogen was started. During this period of time *P. furiosus* produced 73.5 mM $H_2$ (73.5 mmol $H_2$ per liter of liquid culture). This is 1646 ml $H_2$ per liter of liquid culture. So the average $H_2$ production rate was 44 ml per hour and per liter of liquid culture (mL/h$^{-1}$/L$^{-1}$). The maximum $H_2$ production rate measured was 72 ml/h$^{-1}$/L$^{-1}$.

15. *Pyrococcus furiosus* Grows on Starch Containing Waste Materials

*P. furiosus* was grown on 3.0% (w/v) pulp (from potato production) as substrate. Thereby the microorganisms grew to a final cell density of $7.5 \times 10^7$ cells/ml (no pH control, no feed).

16. *Pyrococcus furiosus* Grows on Mixtures of Organic Waste Materials

*P. furiosus* was grown on a mixture of 3.0% (w/v) pulp and 3.0% (v/v) whey. On these substrates *Pyrococcus* grew to a final cell density of $1.4 \times 10^8$ cells/ml (no pH control, no feed). So addition of whey to the pulp substrate resulted in a 2 times higher final cell density.

*P. furiosus* also grew on a mixture of 5.0% (w/v) grain residues and 0.9% (w/v) fish innards. With this substrate mixture a final cell density of $1.0 \times 10^8$ cells/ml was reached (no pH control, no feed).

17. *Pyrococcus furiosus* Grows on Silage

When *P. furiosus* was grown on 5% (w/v) fermented corn/grass silage and 0.5% (w/v) fresh (not fermented) corn silage (same substrate as described at 9.) very good growth was observed. The culture reached a final cell density of $9.7 \times 10^8$ cells/ml. This is about the same value as on pure starch as substrate. This experiment was performed without additional substrate feed but with automatic pH control.

18. Growth of *Pyrococcus furiosus* and *Thermotoga maritima* on the Same Medium In some experiments first growth of *Pyrococcus* was studied at 90° C., if *Pyrococcus* failed to grow or after growth of *Pyrococcus* to $1 \times 10^8$ cells/ml the medium was cooled down to 80° C. and then the same medium was inoculated with *Thermotoga*. On the substrate mixture grain residues and fish innards good growth of *Thermotoga* was observed under these conditions; this indicates that *Thermotoga* grows well in *Pyrococcus* medium.

In addition, when *Pyrococcus* was grown in 100 l scale on starch to a cell density of $1 \times 10^8$ and 30 l of this culture was added to a second reactor containing 30 l sterilized medium with straw and whey as substrate which was inoculated by *Thermotoga maritima*, *Thermotoga* grew to a final cell density of $1 \times 10^9$. This finding indicates that *Thermotoga* can be cultivated in a medium already used for cultivation of *Pyrococcus* as indicated in the flow diagram shown in FIG. 4.

19. Energy Production from Organic Waste Materials by *Thermotoga maritima* in Comparison to Energy Production by a Common Biogas Plant When a mixture of 5% (w/v) fermented corn/grass silage, 0.5% (w/v) fresh (not fermented) corn silage and 8% (w/v) whey was used as substrate, *T. maritima* reached a final cell density of $1.1 \times 10^9$ cells/ml and produced 24.84 mM $H_2$ (no pH control). Since this experiment was conducted in a 100 liter bioreactor, the total amount of produced $H_2$ was 2484 mmol (55.64 liter). Furthermore 16.95 mM (1.018 g/L) acetate was formed. So the total amount of acetate was 1695 mmol (101.8 g).

Using pure fermented corn/grass silage or pure whey as substrate resulted in very poor growth ($6.0 \times 10^6$ cells/ml and $7.0 \times 10^6$ cells/ml respectively). So the major carbon sources and growth factors must be present in the not fermented silage. This is the main substrate in this experiment while fermented silage and whey can be seen as additives (sources of minerals and vitamins).

These facts are the basis for the following calculations:

| | |
|---|---|
| $H_2$ produced per kg of fresh corn silage: | 55.64 l/0.5 kg = 111.3 l/kg |
| $CH_4$ produced by a common biogas plant per kg of fresh corn silage: | 110 l/kg |
| Gross calorific value of $H_2$ (higher heating value): | 11.7 kJ/L |
| Gross calorific value of $CH_4$ (higher heating value): | 36.3 kJ/L |
| Energy produced per kg fresh corn silage by $H_2$ production: | 1302.21 kJ/kg |
| Energy produced per kg of fresh corn silage by methane production: | 3993.00 kJ/kg |

Even more energy can be obtained when acetate produced by *T. maritima* is used as substrate for the methane production in a biogas plant. *T. maritima* produced 1695 mmol acetate out of 0.5 kg corn silage, which can be metabolized to 1695 mmol of $CH_4$ by methanogens in a biogas plant. This corresponds to 37.97 liter $CH_4$ or 1378.24 kJ respectively. So the energy yield of this methanogenic fermentation would be 2756.48 kJ per kg fresh corn silage.

So the total energy yield per kg fresh corn silage would be:

1302.21 kJ/kg+2756.48 kJ/kg=4059 kJ/kg

These data show that the energy yield by $H_2$ production is in a similar range as for $CH_4$ production in a common biogas plants. In the experiment that is the basis of these calculations, no automatic pH control was performed and the fermentation was stopped after 47 hours. Keeping a constant pH value could improve growth while prolonging the fermentation time would allow the bacteria to metabolize all of the substrate. So most likely even more energy can be obtained per kg of fresh corn silage.

When *T. maritima* was grown on the corn silage substrate the generation time was about one hour and 111.28 liter $H_2$ (1302.21 kJ) per kg of silage was produced in two days. In a common biogas plant a typical methanogen has a generation time of about one day and the retention time of substrates is about 30 days for batch processes.

On basis of these values you can compare the performance of energy production by $H_2$ formation versus energy production by $CH_4$ formation:

| | Energy per kg of fresh corn silage | Time to degrade substrate/produce energy | Energy production per day |
|---|---|---|---|
| $CH_4$ production | 3993.0 kJ/kg | 30 days | 133.1 kJ/kg/d (1.54 W/kg) |
| $H_2$ production | 1302.21 kJ/kg | 2 days | 651.1 kJ/kg/d (7.54 W/kg) |

Energy production by $H_2$ formation occurs almost 5 times faster than energy production by $CH_4$ formation. In other words the $H_2$ process can yield the same power (energy per time) as the $CH_4$ process, but it takes just ⅕ of the fermentation/bioreactor volume. These calculations did not include the further utilization of acetate formed during the $H_2$ production process. When acetate is used in a coupled process for $CH_4$ production the energy production is even higher:

| | Energy per kg of fresh corn silage | Time to degrade substrate/produce energy | Energy production per day |
|---|---|---|---|
| $H_2$ production | 1302.21 kJ/kg | 2 days | 651.1 kJ/kg/d (7.54 W/kg) |
| $CH_4$ production by acetate degradation | 2756.48 kJ/kg | 30 days | 91.9 kJ/kg/d (1.06 W/kg) |
| total | 4058.69 kJ/kg | | 743.0 kJ/kg/d (8.6 W/kg) |

20. Combination of a Two-Stage Hydrogen Production Process Coupled to a Methane Production Process As the combination of hydrogen and methane production seems to be promising for effective energy production by utilizing organic waste materials we plan to establish the following three-stage process (see FIG. 4):

1st Stage:

Cellulose and starch containing waste materials are applied as substrates in a bioreactor. In this bioreactor *Pyrococcus furiosus* metabolizes starch and forms $H_2$ and acetate. $H_2$ can be burned immediately for energy production or it can be stored. The outflow of the *Pyrococcus* bioreactor still contains cellulose, as *P. furiosus* can hardly degrade this substrate.

2nd Stage:

The cellulose containing outflow of the 1st stage is used as substrate in a second bioreactor. In this bioreactor *Thermotoga maritima* metabolizes the cellulose and produces $H_2$ and acetate. $H_2$ can be burned immediately for energy production or it can be stored. The acetate containing residues are transferred to the third bioreactor.

3rd Stage:

The acetate containing residues formed the 2nd stage are pumped in a third bioreactor and metabolized by *Methanosarcina thermophile*. This organism converts acetate to methane.

21. Summary of Results

The following tables provide a summary of experimental results.

*Thermotoga maritima*

| Substrate | Maximum cell density | Acetate production | Ethanol production | Period of product formation | Hydrogen production | Period of hydrogen production measured |
|---|---|---|---|---|---|---|
| 0.5% (w/v) starch + 1.0% (w/v) starch feed | $3.5 \times 10^9$ cells/ml | 25.5 mM | 1.9 mM | 43 hours | 50.6 mM | 26 hours |
| 0.5% (w/v) cellulose + 0.5% (w/v) cellulose feed | $1.0 \times 10^8$ cells/ml | 1.3 mM | 0.02 mM | 88 hours | 1.9 mM | 48 hours |
| 5% (w/v) grain residues | $8.0 \times 10^6$ cells/ml | | | | | |
| 5% (w/v) grain residues 10% (v/v) whey | $1.4 \times 10^8$ cells/ml | | | | | |
| 5% (w/v) grain residues 0.9% (w/v) fish innards | $2.0 \times 10^8$ cells/ml | | | | | |
| 3.0% (w/v) pulp (from potato production) | $1.1 \times 10^8$ cells/ml | | | | | |
| 3.0% (w/v) pulp 3.0% (v/v) whey | $1.0 \times 10^8$ cells/ml | | | | | |
| 3.0% (w/v) pulp 1.0% (w/v) fish innards | no growth | | | | | |
| 1.5% (w/v) milled sawdust | $5.6 \times 10^7$ cells/ml | | | | | |
| 1.5% (w/v) sawdust | $1.7 \times 10^7$ cells/ml | | | | | |
| 4% (w/v) whey | $7.0 \times 10^6$ cells/ml | | | | | |
| 1.5% (w/v) sawdust 4% (w/v) whey | $2.8 \times 10^7$ cells/ml | | | | | |
| 4% (w/v) fermented corn/grass silage | $6.0 \times 10^6$ cells/ml | | | | | |
| 5% (w/v) fermented corn/grass silage 0.5% fresh corn silage | $6.3 \times 10^8$ cells/ml | | | | | |
| 5% (w/v) fermented corn/grass silage 0.5% fresh corn silage + 8% (w/v) whey feed | $1.1 \times 10^9$ cells/ml | 17.0 mM | 4.3 mM | 47 hours | 24.8 mM | 27 hours |
| 5% (w/v) fermented corn silage/poultry manure | $1.0 \times 10^7$ cells/ml | | | | | |
| 5% (w/v) fermented corn silage/poultry manure + 4% (w/v) whey feed | $2.0 \times 10^8$ cells/ml | | | | 5.4 mM | 52 hours |
| 5% (w/v) fermented corn silage/poultry manure 4% (w/v) whey | $2.6 \times 10^7$ cells/ml | | | | | |
| 5% (w/v) fermented corn silage/poultry manure 4% (w/v) whey + 12% (w/v) whey feed | $4.0 \times 10^8$ cells/ml | | | | 42.8 mM | 69 hours |

*Pyrococcus furiosus*

| Substrate | Maximum cell density | Acetate production | Ethanol production | Period of product formation | Hydrogen production | Period of hydrogen production measured |
|---|---|---|---|---|---|---|
| 0.5% (w/v) starch + 0.5% (w/v) starch feed | $1.1 \times 10^9$ cells/ml | 39.5 mM | 0.17 mM | 48.5 hours | 73.5 mM | 37 hours |
| 5% (w/v) grain residues | no growth | | | | | |
| 5% (w/v) grain residues 10% (v/v) whey | no growth | | | | | |
| 5% (w/v) grain residues 0.9% (w/v) fish innards | $1.0 \times 10^8$ cells/ml | | | | | |
| 3.0% (w/v) pulp (from potato production) | $7.5 \times 10^7$ cells/ml | | | | | |
| 3.0% (w/v) pulp 3.0% (v/v) whey | $1.4 \times 10^8$ cells/ml | | | | | |
| 3.0% (w/v) pulp 1.0% (w/v) fish innards | no growth | | | | | |
| 5% (w/v) fermented corn/grass silage 0.5% fresh corn silage | $9.7 \times 10^8$ cells/ml | | | | | |

22. Initial Experiments with *Thermotoga* MH-1

By searching for *Thermotoga* strains, capable of degrading cellulose more efficiently than *T. maritima*, we found the promising strain MH-1. Before large scale fermentations were performed, growth of T. MH-1 was tested in small scale. *T. maritima* and T. MH-1 were both inoculated twice in 20 ml MM-I medium containing 0.5% cellulose and 0.05% yeast extract. After 64 hours incubation, the cell densities of the four cultures were determined and the gas phases of the serum bottles were analyzed for hydrogen.

The final cell densities of the MH-1 cultures were higher than those of *T. maritima*. These higher cell densities came along with higher $H_2$ contents in the gas phase of the MH-1 cultures. T. MH-1 was deposited with the DSMZ and given Accession No. DSM 22925.

| | *T. maritima* | | T. MH-1 | |
|---|---|---|---|---|
| Sample | 1 | 2 | 3 | 4 |
| Cell Density | $1.1 \times 10^8$ cells/ml | $9.8 \times 10^7$ cells/ml | $1.5 \times 10^8$ cells/ml | $1.8 \times 10^8$ cells/ml |
| $H_2$ content of gas phase | 0.83% | 0.88% | 1.18% | 1.12% |

23. Comparison of *Thermotoga maritima* and *Thermotoga* MH-1 on Different (Waste) Substrates in 100 liter Fermentations

*Thermotoga* MH-1 was grown in a 100 liter fermenter on MM-I medium with 0.05% yeast extract on different substrates. The results were compared to experiments with *Thermotoga maritima* where the same substrates were used. The results are listed below.

| Substrates | Strain | Maximum cell density [cells/ml] | Volumetric hydrogen production rate | $H_2$ yield per kg substrate | Acetate yield per kg substrate |
|---|---|---|---|---|---|
| Straw + Whey | *T. maritima* | $2.2 \times 10^9$ | 47 ml l$^{-1}$ h$^{-1}$ | 61 liter | 82 g |
| | T. MH-1 | $3.7 \times 10^9$ | 112 ml l$^{-1}$ h$^{-1}$ | 96 liter | 148 g |
| Potato pulp + Whey | *T. maritima* | $1.4 \times 10^9$ | 120 ml l$^{-1}$ h$^{-1}$ | 24 liter | 27 g |
| | T. MH-1 | $3.1 \times 10^9$ | 229 ml l$^{-1}$ h$^{-1}$ | 40 liter | 41 g |

T. MH-1 showed significantly better growth, hydrogen production and acetate production on both substrates. So this strain could be a candidate for large scale hydrogen production from (waste) biomass.

was 0.07 mmol×l$^{-1}$×h$^{-1}$ (total amount of ethanol produced: 14.8 g) while during the experiment with 3 kg straw and 18% whey only 0.01 mmol×l$^{-1}$×h$^{-1}$ ethanol were produced (total amount of ethanol produced: 4.2 g).

| Substrate | 1.5% (w/v) straw | 3.0% (w/v) straw | 3.0% (w/v) straw |
|---|---|---|---|
| Additives | 0.05% (w/v) yeast extract | 0.05% (w/v) yeast extract | 0.05% (w/v) yeast extract |
| Whey feed | 9% (w/v) | 12% (w/v) | 18% (w/v) |
| Straw:whey ratio | 1:6 | 1:4 | 1:6 |
| H$_2$ produced per kg substrate | 94.3 l × kg$^{-1}$ | 66.3 l × kg$^{-1}$ | 89.1 l × kg$^{-1}$ |
| Final cell density | 3.70 × 10$^9$ cells/ml | 3.19 × 10$^9$ cells/ml | 2.94 × 10$^9$ cells/ml |
| Maximum H$_2$ production rate | 112 ml×l$^{-1}$×h$^{-1}$ / 4.6 mmol×l$^{-1}$×h$^{-1}$ | 88 ml×l$^{-1}$×h$^{-1}$ / 3.6 mmol×l$^{-1}$×h$^{-1}$ | 110 ml×l$^{-1}$×h$^{-1}$ / 4.5 mmol×l$^{-1}$×h$^{-1}$ |
| Total H$_2$ production | 144.5 l | 198.8 l | 267.2 l |
| H$_2$ production ceased after: | 34 h | 43 h | 47 h |
| Acetate production rate | 46 mg×l$^{-1}$×h$^{-1}$ / 0.08 mmol×l$^{-1}$×h$^{-1}$ | 52 mg×l$^{-1}$×h$^{-1}$ / 0.9 mmol×l$^{-1}$×h$^{-1}$ | 51 mg×l$^{-1}$×h$^{-1}$ / 0.9 mmol×l$^{-1}$×h$^{-1}$ |
| Ethanol production rate | 3.1 mg×l$^{-1}$×h$^{-1}$ / 0.07 mmol×l$^{-1}$×h$^{-1}$ | 1.3 mg × 1$^{-1}$ × h$^{-1}$ / 0.03 mmol × 1$^{-1}$ × h$^{-1}$ | 0.7 mg×l$^{-1}$×h$^{-1}$ / 0.01 mmol×l$^{-1}$×h$^{-1}$ |

24. *Thermotoga* MH-1 Grows on Straw as Substrate

T. MH-1 was grown in a 100 liter bioreactor on MM-I medium with 0.05% yeast extract and straw as substrate. Straw was used in concentrations of 1.5% (w/v) and 3.0% (w/v) respectively. The results are listed below.

| Organism | *Thermotoga* MH-1 | |
|---|---|---|
| Substrate | 1.5% (w/v) straw | 3.0% (w/v) straw |
| Maximum cell density | 7.5 × 10$^8$ cells/ml | 1.4 × 10$^9$ cells/ml |
| Maximum hydrogen production rate | 602 ml × d$^{-1}$ × l$^{-1}$ | 1175 ml × d$^{-1}$ × l$^{-1}$ |
| Hydrogen per kg straw | 12.3 l × kg$^{-1}$ | 15.1 l × kg$^{-1}$ |
| Acetate per kg straw | 36.4 g × kg$^{-1}$ | 29.9 g × kg$^{-1}$ |

Cells density and maximum hydrogen production rate of T. MH-1 doubled when the amount of straw was doubled. In contrast the amount of hydrogen per kg substrate increased just slightly and the amount of acetate per kg substrate decreased a little bit.

25. Growth of *Thermotoga* MH-1 on Straw with Additional Whey Feed

T. MH-1 was grown in a 100 liter bioreactor on MM-I medium with 0.05% yeast extract and straw as substrate. In addition whey was added when the cultures were in the exponential growth phase. These experiments were performed with different straw and whey concentrations.

The results in the table below indicate, that the hydrogen yield is dependent on the straw:whey ratio rather than on the straw concentration. Using a straw:whey ratio of 1:6 resulted in a hydrogen yield of 94.3 l×kg$^{-1}$ (1.5% straw and 9% whey) and 89.1 l×kg$^{-1}$ (3.0% straw and 18% whey) respectively, while a straw:whey ratio of 1:4 yielded only 66.3 l×kg$^{-1}$. So T. MH-1 is clearly able to produce more hydrogen when a straw:whey ratio of 1:6 is used. The table below shows also that the total amount of hydrogen produced was twice as high when the amount of substrates was doubled. An interesting difference was observed with respect to ethanol production. With 1.5 kg of straw and 9% whey the ethanol production rate 26. Fermentation at High Cell Densities The methods and systems described herein have been useful in establishing fermentation cultures at high cell density. The results on different substrates are summarized below.

| | *T. maritima* | T. MH-1 |
|---|---|---|
| Medium | MM-1 | MM-1 |
| Substrate (w/v) | 3.5% potato pulp | 3.5% potato pulp |
| Feed (w/v) | 3.5% pulp; 5.0% whey | 3.5% pulp; 5.1% whey |
| Total amount substrate | 7.0 kg pulp | 7.0 kg pulp |
| Additives (w/v) | 0.5% yeast extract | 0.5% yeast extract |
| Generation time | 1.5 hours | 1.9 hours |
| Cell density | 1.4 × 10$^9$ cells/ml | 3.1 × 10$^9$ cells/ml |

| | *T. maritima* | *P. furiosus* | T. MH-1 |
|---|---|---|---|
| Medium | MM-1 | ½ SME | MM-1 |
| Substrate (w/v) | 0.5% starch | 0.5% starch | 0.5% starch |
| Feed (w/v) | 2x 0.5% starch | 1x 0.5% starch | |
| Additives (w/v) | 0.5% yeast extract | 0.5% yeast extract | 0.5% yeast extract |
| Generation time | 1.1 hours | 1.3 hours | 2.1 hours |
| Cell density | 3.5 × 10$^9$ cells/ml | 1.1 × 10$^9$ cells/ml | 5.16 × 10$^9$ cells/ml |

| | *T. maritima* | MH-1 |
|---|---|---|
| Medium | MM-1 | MM-1 |
| Substrate (w/v) | 1.5% straw | 1.5% straw |
| Feed (w/v) | 10.00% whey | 9.4% whey |
| Substrate for calculations | 1.5 kg straw | 1.5 kg straw |
| Additives (w/v) | 0.05% yeast extract | 0.05% yeast extract |
| Cell density | 2.24 × 10$^9$ cells/ml | 3.7 × 10$^9$ cells/ml |

27. *Thermotoga* MH-1 Grows on Whey as Substrate

T. MH-1 was grown in a 100 liter bioreactor on MM-I medium with 0.05% yeast extract and 8% (w/v) whey as substrate. *Thermotoga* strain MH-1 was able to grow on whey alone in contrast to *Thermotoga maritima*. The maximum production rate for hydrogen as well as the total amounts of hydrogen and acetate produced are listed below.

| | |
|---|---|
| Substrate | 8.0% (w/v) whey |
| Additives | 0.05% (w/v) yeast extract |
| Final cell density | $2.5 \times 10^9$ cells/ml |
| Hydrogen | |
| Total amount produced | $1584 \text{ ml} \times l^{-1}$ (64.7 mM) |
| Maximum production rate | $67 \text{ ml} \times l^{-1} \times h^{-1}$ |
| Amount of $H_2$ produced per kg (moist) substrate | $20 \text{ l} \times kg^{-1}$ |
| Acetate | |
| Total amount produced | $1786 \text{ mg} \times l^{-1}$ (29.7 mM) |
| Amount of acetate produced per kg (moist) substrate | $22 \text{ g} \times kg^{-1}$ |

28. *Thermotoga* MH-1 Grows on a Mixture of Pig Manure and Whey

On pig manure as the only substrate growth and hydrogen production of T. MH-1 was very poor. But on 3% (w/v) pig manure with an additional 8% (w/v) whey feed, T. MH-1 grew to a final cell density of $4.1 \times 10^9$ cells/ml. This experiment was conducted in a 100 liter fermenter with MM-I medium and 0.05% yeast extract. The results are listed below.

| | |
|---|---|
| Substrate | 3.0% (w/v) pig manure |
| Additives | 0.05% (w/v) yeast extract |
| Whey feed | 8% (w/v) |
| Final cell density | $4.1 \times 10^9$ cells/ml |
| Hydrogen | |
| Total amount produced | $1637 \text{ ml} \times l^{-1}$ (66.9 mM) |
| Maximum production rate | $104 \text{ ml} \times l^{-1} \times h^{-1}$ |
| Amount of $H_2$ produced per kg (moist) substrate | $55 \text{ l} \times kg^{-1}$ |
| Acetate | |
| Total amount produced | $2146 \text{ mg} \times l^{-1}$ (35.7 mM) |
| Amount of acetate produced per kg (moist) substrate | $71.5 \text{ g} \times kg^{-1}$ |

When pig manure and whey were used as substrates, the total amount of $H_2$ and acetate produced was only slightly higher, compared to the fermentation with whey as the only substrate (see section 27). But the cell density and the hydrogen production rate was much higher.

29. *Thermotoga* MH-1 Grows on Fresh Corn Silage

T. MH-1 was grown in a 100 liter bioreactor on MM-I medium with 0.05% yeast extract and 3% (w/v) fresh corn silage as substrate. In one experiment an additional 12% (w/v) whey feed was performed.

The addition of whey caused a 2.3 fold increase in the hydrogen production rate compared to the same experiment without whey feed. The total amounts of products were also significantly higher when whey was added. The cell densities where almost the same in both experiments.

| | Duration of experiment | |
|---|---|---|
| | 41.5 hours | 64.5 hours |
| Substrate | 3.0% (w/v) corn silage | 3.0% (w/v) corn silage |
| Additives | 0.05% (w/v) yeast extract | 0.05% (w/v) yeast extract |
| Whey feed | — | 12.3% (w/v) |
| Final cell density | $4.5 \times 10^9$ cells/ml | $4.9 \times 10^9$ cells/ml |
| Hydrogen | | |
| Total amount produced | $1324 \text{ ml} \times l^{-1}$ (54.1 mM) | $3103 \text{ ml} \times l^{-1}$ (126.6 mM) |
| Maximum production rate | $112 \text{ ml} \times l^{-1} \times h^{-1}$ | $156 \text{ ml} \times l^{-1} \times h^{-1}$ |
| Amount of $H_2$ produced per kg (moist) substrate | $44 \text{ l} \times kg^{-1}$ | $103 \text{ l} \times kg^{-1}$ |
| Acetate | | |
| Total amount produced | $1831 \text{ mg} \times l^{-1}$ (30.5 mM) | $3905 \text{ mg} \times l^{-1}$ (65.0 mM) |
| Amount of acetate produced per kg (moist) substrate | $61 \text{ g} \times kg^{-1}$ | $130 \text{ g} \times kg^{-1}$ |

30. Continuous Fermentation with *Thermotoga* MH-1 on Pure Starch as Substrate T. MH-1 was grown on MM-I medium in continuous mode in a 10 liter bioreactor. As no appropriate control systems were available, it was not possible to keep a stable steady state. But the results show, that the productivity of T. MH-1 can be improved significantly when cultivated in continuous mode.

| Fermentation mode | BATCH | CONTINUOUS |
|---|---|---|
| Substrate | 1.5% (w/v) starch | 1.0% (w/v) starch |
| Additives | 0.05% (w/v) yeast extract | 0.05% (w/v) yeast extract |
| Whey feed | 7.9% (w/v) | — |
| Maximum cell density | $2.84 \times 10^9$ cells/ml | $2.7 \times 10^9$ cells/ml |
| Maximum $H_2$ production rate | $\dfrac{84 \text{ ml} \times l^{-1} \times h^{-1}}{3.4 \text{ mmol} \times l^{-1} \times h^{-1}}$ | $\dfrac{147 \text{ ml} \times l^{-1} \times h^{-1}}{6.0 \text{ mmol} \times l^{-1} \times h^{-1}}$ |
| Starch consumption rate | $261 \text{ mg} \times l^{-1} \times h^{-1}$ | $607 \text{ mg} \times l^{-1} \times h^{-1}$ |
| Acetate production rate | $\dfrac{91 \text{ mg} \times l^{-1} \times h^{-1}}{1.5 \text{ mmol} \times l^{-1} \times h^{-1}}$ | $\dfrac{198 \text{ mg} \times l^{-1} \times h^{-1}}{3.3 \text{ mmol} \times l^{-1} \times h^{-1}}$ |
| Ethanol production rate | $\dfrac{4 \text{ mg} \times l^{-1} \times h^{-1}}{0.08 \text{ mmol} \times l^{-1} \times h^{-1}}$ | $\dfrac{102 \text{ mg} \times l^{-1} \times h^{-1}}{2.2 \text{ mmol} \times l^{-1} \times h^{-1}}$ |

The maximum cell densities in batch and in continuous mode were almost the same. But the $H_2$, acetate and ethanol production rates were significantly higher in the continuous fermentation. So a significant increase in productivity can also be expected for biomass fermentations in continuous mode.

31. Growth of *Thermotoga* MH-1 on Seaweed as a Substrate in 20 Ml Cultures

Figure 5:
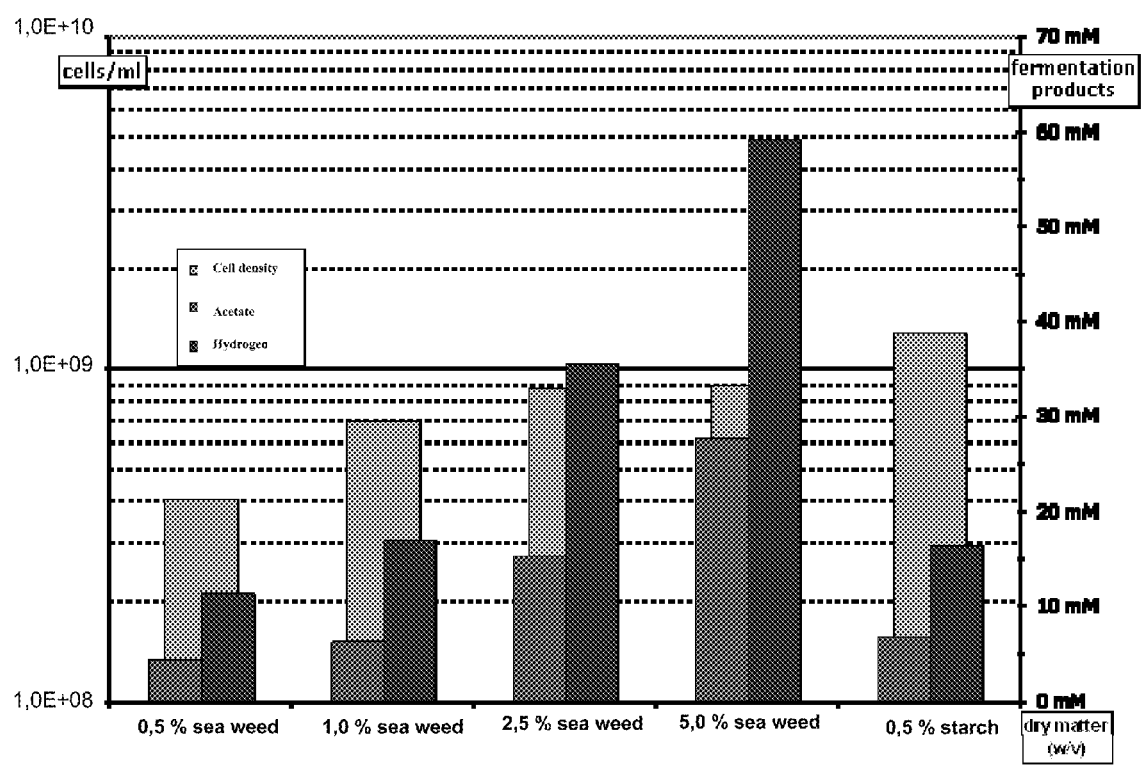
FIG. 5 provides a graph summarizing the growth of *Thermotoga* MH-1 on seaweed in 20 ml cultures.

*Thermotoga* MH-1 was grown in 120 ml serum bottles with 20 ml MM-I medium (+0.05% yeast extract) and different amounts of seaweed (*Laminaria* sp. Brown algae from Norway). For comparison T. MH-1 was also inoculated in MM-I medium with 0.05% pure starch. The results are listed below and illustrated in FIG. 5.

| Substrate (w/v dry matter) | Final cell density [cells/ml] | Hydrogen production per liter liquid culture | $H_2$ production compared to starch as substrate | Acetate production per liter liquid culture | Acetate production compared to starch as substrate |
|---|---|---|---|---|---|
| 0.5% seaweed | $4.0 \times 10^8$ | 276 ml × $l^{-1}$ (11.3 mM) | 70% | 254 mg × $l^{-1}$ (4.2 mM) | 63% |
| 1.0% seaweed | $6.9 \times 10^8$ | 410 ml × $l^{-1}$ (16.7 mM) | 103% | 371 mg × $l^{-1}$ (6.2 mM) | 92% |
| 2.5% seaweed | $8.7 \times 10^8$ | 866 ml × $l^{-1}$ (35.4 mM) | 218% | 909 mg × $l^{-1}$ (15.1 mM) | 226% |
| 5.0% seaweed | $8.9 \times 10^8$ | 1445 ml × $l^{-1}$ (59.1 mM) | 364% | 1651 mg × $l^{-1}$ (27.5 mM) | 410% |
| 0.5% starch | $1.3 \times 10^9$ | 397 ml × $l^{-1}$ (16.2 mM) | 100% | 403 mg × $l^{-1}$ (6.7 mM) | 100% |

T. MH-1 showed best growth on pure starch as substrate, but the acetate and hydrogen production was much better on seaweed when used in concentrations higher than 1.0%. This result cannot be explained by substrate deficiency in the 0.5% starch medium, as not all of the starch was consumed when the experiment was stopped. So obviously seaweed is an excellent substrate for T. MH-1 and is considered to be used for large scale applications.

32. Selection of the Low Salt Adapted Strain *Thermotoga* MH-2

*Thermotoga* MH-1 is usually cultivated on MM-I medium containing 0.7% (w/v) NaCl. For T. MH-1 the high salt concentration is necessary for good growth. To adapt T. MH-1 to low salt concentrations (≦0.2%) it was cultivated on 20 ml MM-I medium in 120 ml serum bottles with stepwise decreasing NaCl concentrations. First inoculation was on 0.5% NaCl medium, which was used as pre-culture for the next inoculation on 0.5% NaCl medium and so on. The transfers with corresponding NaCl concentrations are listed in the table below.

| Transfers | NaCl concentration |
|---|---|
| 1-3 | 0.50% NaCl |
| 4-7 | 0.30% NaCl |
| 8-15 | 0.20% NaCl |

Figure 6:
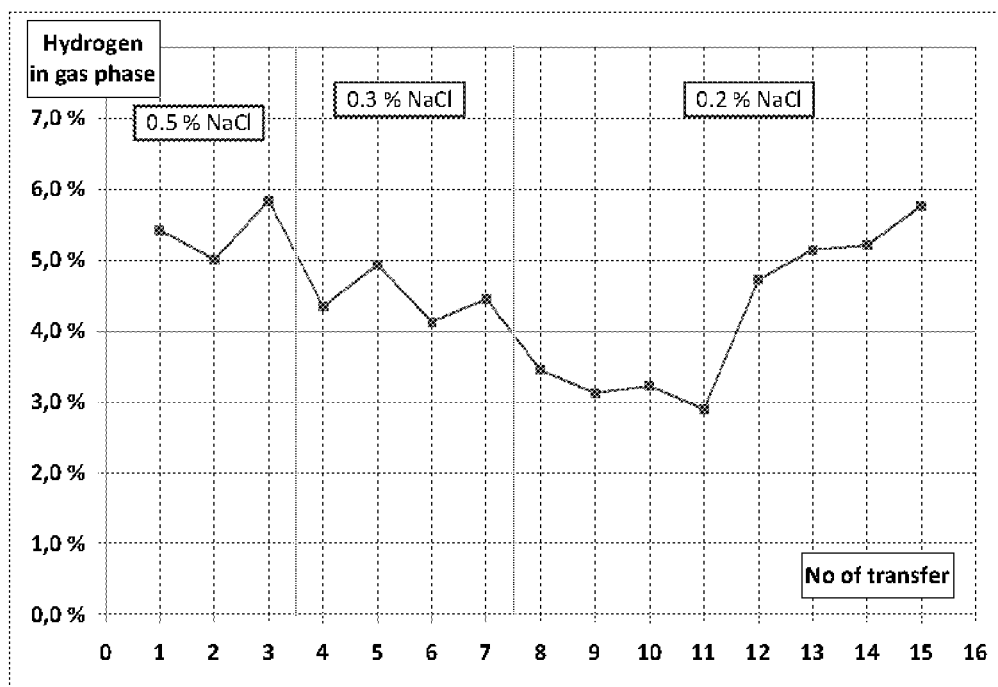
FIG. 6 provides a graph of hydrogen production of T. MH-1 on media with different NaCl concentrations.
Figure 7:
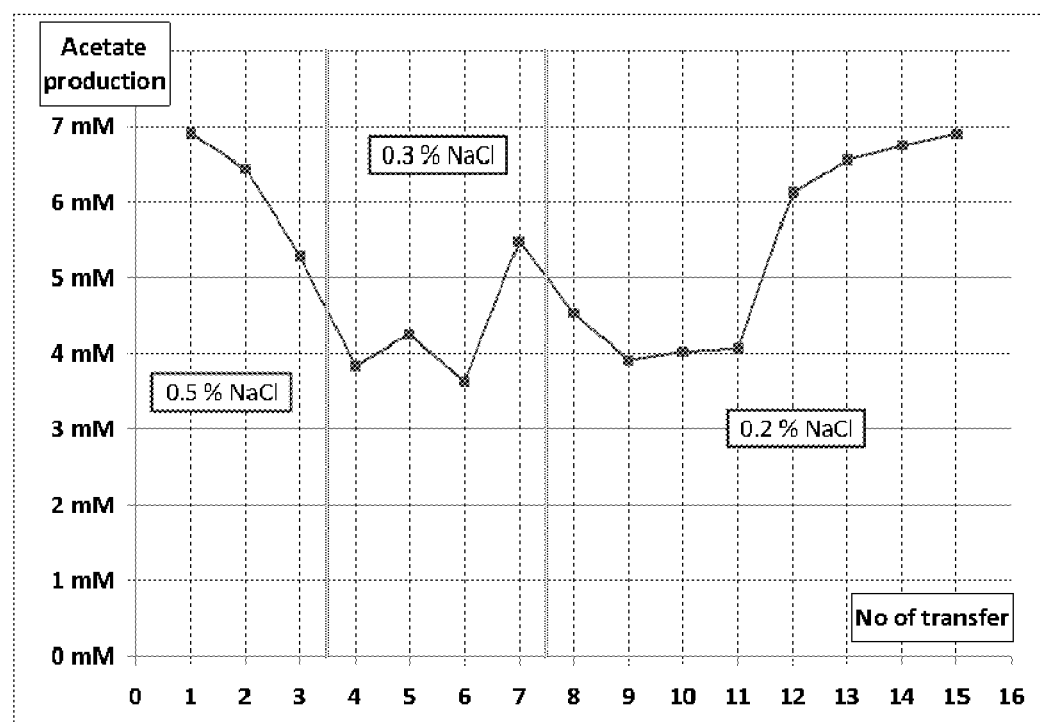
FIG. 7 provides a graph of acetate production of T. MH-1 on media with different NaCl concentrations.

All cultures were incubated at 80° C. for 17 hours. Then the hydrogen content of the gas phase and the acetate concentration in the liquid phase were measured (see table below and FIGS. 6 and 7). Hydrogen and acetate production decreased with decreasing NaCl concentrations. But after the 11$^{th}$ transfer the hydrogen and acetate concentrations increased. This finding suggests that due the selection pressure (low NaCl concentration) a mutant was established, which was better adapted to the low salt growth conditions. This mutant was designated as *Thermotoga* MH-2 and deposited with the DSMZ and given Accession No. DSM 22926.

| | Hydrogen content of the gas phase | Acetate production |
|---|---|---|
| 1 | 5.43% | 6.91 mM |
| 2 | 5.01% | 6.44 mM |
| 3 | 5.84% | 5.29 mM |
| 4 | 4.35% | 3.83 mM |
| 5 | 4.94% | 4.25 mM |
| 6 | 4.13% | 3.62 mM |
| 7 | 4.45% | 5.48 mM |
| 8 | 3.44% | 4.53 mM |
| 9 | 3.12% | 3.92 mM |
| 10 | 3.22% | 4.03 mM |
| 11 | 2.90% | 4.07 mM |
| 12 | 4.72% | 6.13 mM |
| 13 | 5.15% | 6.56 mM |
| 14 | 5.21% | 6.74 mM |
| 15 | 5.77% | 6.90 mM |

For this experiment the following medium was used.

MM-I-Medium (V08/11HT with Starch and Yeast Extract)

| Substance | Amount | Concentration |
|---|---|---|
| SME | 250.0 ml | |
| $KH_2PO_4$ | 0.5 g | 3.67 mM |
| $NH_4Cl$ | 0.5 g | 9.35 mM |
| $NaHCO_3$ | 0.1 g | 1.19 mM |
| Starch | 5.0 g | |
| Yeast extract | 0.5 g | |
| Wolfe's mineral elixir 10x/pH 1.0 | 1.5 ml | |
| Resazurin, 0.1% | 1.0 ml | |
| $Na_2S \times 7\text{-}9H_2O$ | 0.5 g | |
| $H_2O$ 2x distilled, add to a final volume of | 1000.0 ml | |

SME

| Substance | Amount | Concentration |
|---|---|---|
| (NaCl)[1] | (27.7 g) | (473.99 mM) |
| $MgSO_4 \times 7H_2O$ | 7.0 g | 28.4 mM |
| $MgCl_2 \times 6H_2O$ | 5.5 g | 27.1 mM |
| $CaCl_2 \times 2H_2O$ | 0.75 g | 5.1 mM |
| KCl | 0.65 g | 8.7 mM |
| NaBr | 0.1 g | 0.97 mM |
| $H_3BO_3$ | 0.03 g | 0.49 mM |
| $SrCl_2 \times 6H_2O$ | 0.015 g | 0.056 mM |
| KJ-solution, 0.05% | 0.1 ml | 0.30 μM |
| $H_2O$ 2x distilled, add to a final volume of | 1000.0 ml | |

[1] NaCl was omitted for this experiment and the desired NaCl concentrations in the serum bottles were adjusted by adding NaCl from a 20% or a 5% stock solution.

Wolfe's mineral elixir 10×/pH 1.0 (V08/11HT)

| Substance | Amount | Concentration |
|---|---|---|
| $MgSO_4 \times 7H_2O$ | 30.0 g | 121.70 mM |
| $MnSO_4 \times H_2O$ | 5.0 g | 29.60 mM |
| NaCl | 10.0 g | 171.10 mM |
| $FeSO_4 \times 7H_2O$ | 3.8 g | 13.67 mM |
| $CoSO_4 \times 7H_2O$ | 1.8 g | 6.40 mM |
| $CaCl_2 \times 2H_2O$ | 1.0 g | 6.80 mM |
| $ZnSO_4 \times 7H_2O$ | 1.8 g | 6.30 mM |
| $CuSO_4 \times 5H_2O$ | 0.1 g | 0.40 mM |
| $KAl(SO_4)_2 \times 12H_2O$ | 0.18 g | 0.38 mM |
| $H_3BO_3$ | 0.1 g | 1.62 mM |
| $Na_2MoO_4 \times 2H_2O$ | 0.1 g | 0.41 mM |
| $(NH_4)_2Ni(SO_4)_2 \times 6H_2O$ | 2.80 g | 7.09 mM |
| $Na_2WO_4 \times 2H_2O$ | 3.0 g | 9.09 mM |
| $Na_2SeO_4$ | 0.1 g | 0.53 mM |
| $H_2O$ 2x distilled, add to a final volume of | 1000.0 ml | | adjust pH to 1.0 with $H_2SO_4$

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The invention claimed is:

1. A process comprising:
   treating a biomass with a hyperthermophilic organism selected from the group consisting of microorganisms MH-1 (Accession No. DSM 22925) and MH-2 (Accession No. DSM 22926) under conditions such that at least one degradation product is produced.

2. The process of claim 1, further comprising the step of separating at least one degradation product from said biomass.

3. The process of claim 1, further comprising the step of converting said degradation product into heat or electricity.

4. The process of claim 1, wherein said biomass is selected from the group consisting of sewage, agricultural waste products, straw, corn stover, brewery grain by-products, food waste, organic industry waste, forestry waste, crops, grass, seaweed, plankton, algae, fish, fish waste, and combinations thereof.

5. The process of claim 1, wherein said biomass is seaweed or a mixture of seaweed and at least one other biomass.

6. The process of claim 1, wherein at least one degradation product is selected from the group consisting of hydrogen, acetate, methane and ethanol and combinations thereof.

7. The process of claim 1, wherein said microorganism is MH-1 (Accession No. DSM 22925) and said biomass is degraded in the presence of a cell density of said microorganism of greater than $10^9$ cells/ml.

8. The process of claim 1, wherein said degradation product is acetate and further comprising the step of feeding said acetate to methanogenic bacteria under conditions such that said acetate is converted to methane.

9. The process of claim 1, further comprising the step of feeding at least one degradation product to a culture system comprising algae under conditions such that the growth of said algae is enhanced.

10. The process of claim 9, wherein said degradation product is acetate.

11. The process of claim 9, further comprising the step of producing fatty acids from said algae.

12. The process of claim 1, wherein said microorganism is MH-2 (Accession No. DSM 22926) and said biomass is degraded at a salt concentration of less than about 0.2%.

13. The process of claim 1, wherein said conditions comprising maintaining said microorganism in a stationary phase.

14. An isolated microorganism designated strain MH-1 (Accession No. DSM 22925).

15. An isolated microorganism designated strain MH-2 (Accession No. DSM 22926).

* * * * *